United States Patent
Huang et al.

(10) Patent No.: US 11,452,442 B2
(45) Date of Patent: Sep. 27, 2022

(54) SYSTEMS AND METHODS FOR AUTOMATED WIDEFIELD OPTICAL COHERENCE TOMOGRAPHY ANGIOGRAPHY

(71) Applicant: Oregon Health & Science University, Portland, OR (US)

(72) Inventors: David Huang, Portland, OR (US); Gangjun Liu, Portland, OR (US); Yali Jia, Portland, OR (US)

(73) Assignee: OREGON HEALTH & SCIENCE UNIVERSITY, Portland, OR (US)

(*) Notice: Subject to any disclaimer, the term of this patent is extended or adjusted under 35 U.S.C. 154(b) by 701 days.

(21) Appl. No.: 16/308,901

(22) PCT Filed: Jun. 15, 2017

(86) PCT No.: PCT/US2017/037622
§ 371 (c)(1),
(2) Date: Dec. 11, 2018

(87) PCT Pub. No.: WO2017/218738
PCT Pub. Date: Dec. 21, 2017

(65) Prior Publication Data
US 2019/0150729 A1    May 23, 2019

Related U.S. Application Data

(60) Provisional application No. 62/350,526, filed on Jun. 15, 2016.

(51) Int. Cl.
*A61B 3/10*    (2006.01)
*A61B 5/00*    (2006.01)
(Continued)

(52) U.S. Cl.
CPC ............ *A61B 3/102* (2013.01); *A61B 3/0091* (2013.01); *A61B 3/10* (2013.01); *A61B 3/1241* (2013.01);
(Continued)

(58) Field of Classification Search
CPC ......... A61B 3/102; A61B 3/10; A61B 3/0091; A61B 3/1241; A61B 3/12; A61B 3/1233;
(Continued)

(56) References Cited

U.S. PATENT DOCUMENTS 5,784,148 A * 7/1998 Heacock .............. A61B 3/1025
                                                                  351/206
2003/0199769 A1   10/2003 Podoleanu et al.
(Continued)

FOREIGN PATENT DOCUMENTS

| WO | WO-2006116317 A1 | * | 11/2006 | ........... A61B 3/1005 |
| WO | WO-2010117386 A1 | * | 10/2010 | ............. A61B 3/032 |
| WO | WO-2015134571 A1 | * | 9/2015 | ............. A61B 3/102 |

OTHER PUBLICATIONS

Kari V. Vienola, Boy Braaf, Christy K. Sheehy, Qiang Yang, Pavan Tiruveedhula, David W. Arathorn, Johannes F. de Boer, and Austin Roorda, "Real-time eye motion compensation for OCT imaging with tracking SLO," Biomed. Opt. Express 3, 2950-2963 (Year: 2012).*

*Primary Examiner* — Travis S Fissel
(74) *Attorney, Agent, or Firm* — Schwabe Williamson & Wyatt, P.C.

(57) ABSTRACT

Disclosed are systems and methods for generating wide-field optical coherence tomography angiography (OCTA) images. In embodiments, multiple OCTA scans of a sample are automatically acquired at overlapping locations. The systems and methods include functionality to adaptively control the scanning procedure such that eye blink and eye motion events are detected in real time and accounted for during 3D
(Continued)

scan acquisition. Also disclosed are methods for detecting and correcting motion-related artifacts in OCTA datasets which allow for the longer scan times over larger fields of view required for wide-field imaging. These methods may include division of en face angiogram images into a set of motion-free parallel strips, and application of gross and fine registration methods to align overlapping strips into a motion-corrected composite image. A series of overlapping motion-corrected composite images may be combined into a larger montage to enable wide-field OCTA imaging using multiple OCTA scans.

32 Claims, 23 Drawing Sheets

(51) Int. Cl.
  *A61B 3/00*   (2006.01)
  *A61B 3/12*   (2006.01)
  *A61B 5/02*   (2006.01)
  *A61B 5/11*   (2006.01)
(52) U.S. Cl.
  CPC ........ *A61B 5/0066* (2013.01); *A61B 5/02007* (2013.01); *A61B 5/1128* (2013.01); *A61B 5/6814* (2013.01); *A61B 5/721* (2013.01); *A61B 5/7207* (2013.01); *A61B 5/7214* (2013.01)
(58) Field of Classification Search
  CPC . A61B 5/7207; A61B 5/0066; A61B 5/02007; A61B 5/1128; A61B 5/6814; A61B 5/721; A61B 5/7214; A61B 5/0073

USPC .......................................... 351/205, 206, 211
See application file for complete search history.

(56) References Cited

U.S. PATENT DOCUMENTS

| | | | |
|---|---|---|---|
| 2007/0291277 A1* | 12/2007 | Everett | G01N 21/4795 356/497 |
| 2010/0220334 A1* | 9/2010 | Condit | G02B 3/12 356/497 |
| 2011/0267340 A1* | 11/2011 | Kraus | G06T 7/248 345/419 |
| 2011/0274351 A1* | 11/2011 | Tsukada | H04N 1/628 382/167 |
| 2012/0033181 A1* | 2/2012 | Koizumi | A61B 3/152 351/208 |
| 2013/0010259 A1* | 1/2013 | Carnevale | A61B 3/102 351/209 |
| 2013/0176532 A1* | 7/2013 | Sharma | A61B 3/102 351/206 |
| 2014/0073917 A1 | 3/2014 | Huang et al. | |
| 2014/0228681 A1* | 8/2014 | Jia | G01B 9/02045 600/425 |
| 2014/0268167 A1* | 9/2014 | Friedman | G06T 7/12 356/479 |
| 2015/0109579 A1* | 4/2015 | Orlowski | A61B 3/102 351/246 |
| 2015/0124219 A1* | 5/2015 | Horn | A61B 3/102 351/208 |

\* cited by examiner

SYSTEMS AND METHODS FOR AUTOMATED WIDEFIELD OPTICAL COHERENCE TOMOGRAPHY ANGIOGRAPHY

CROSS REFERENCE TO RELATED APPLICATION

The present application claims priority to U.S. Provisional Patent Application No. 62/350,526, titled "SYSTEMS AND METHODS FOR AUTOMATED WIDEFIELD OPTICAL COHERENCE TOMOGRAPHY ANGIOGRAPHY," filed Jun. 15, 2016, the disclosure of which is hereby incorporated by reference in its entirety.

ACKNOWLEDGEMENT OF GOVERNMENT SUPPORT

This invention was made with government support under EY023285, EY024544, and DK104397 awarded by the National Institutes of Health. The government has certain rights in the invention.

FIELD

Generally, the field involves methods of imaging using optical coherence tomography. In particular, the field involves methods of visualizing blood flow using optical coherence tomography.

BACKGROUND

Optical coherence tomography angiography (OCTA) detects blood flow within an otherwise static tissue by using the motion of blood cells as an intrinsic contrast mechanism. OCTA requires the acquisition of repeated cross-sectional images (B-scans) at the same location to assess the variation in OCT signal, for example by decorrelation or other methods, of each pixel. Acquisition of a typical volumetric OCTA data requires high-speed OCT technology. To date, limited OCT system speeds have imposed on OCTA a limited field of view. In order to extend OCTA to wide field applications, high speed OCT technology is essential. However, the sensitivity of OCT is limited by the maximum permissible incident power on the eye set by the American National Standard. As a result, there is a tradeoff between the speed of OCT systems and their sensitivity. Operating at high imaging speeds requires short exposure times, which translates into less light collection per scan and decreased sensitivity. Therefore, in order to retain good image quality, speed cannot be increased indefinitely. SS-OCT speeds up to 200 kHz appear to provide adequate OCT signal in patients.

The sensitivity of OCTA to blood flow is also related to the time interval between adjacent B-scans, with a longer time interval preferred for OCTA imaging of small vasculature. These constraints combine to limit the speed of OCTA systems and the field of view that can be covered in a single scan. To achieve a wide field of view, a montage approach using multiple scans having a smaller field of view has been demonstrated. Although effective, the data acquisition for multiple scans, realignment after changing the fixation target, and processing of these data to get a single wide-field OCTA image is cumbersome and time-consuming. Thus, there is a need in the art for more effective techniques to enable wide-field OCTA to be practiced in a clinical setting.

BRIEF DESCRIPTION OF THE SEVERAL VIEWS OF THE DRAWINGS

FIG. 8A is an en face mean projection image of OCT reflectance. FIG. 8B shows the bias field resulting from the application of a Gaussian filter to the en face OCT reflectance image in FIG. 8A.

FIG. 10A is an en face OCTA image after bias field correction. FIG. 10B is an en face OCTA image after the removal of large eye movements. FIG. 10C is an en face OCTA image enhanced by the local histogram equalization and Gabor filter. FIG. 10D shows six micro-saccade-free strips.

FIG. 11A is a reference strip in a zero-padded matrix. FIG. 11B is a moving strip in a zero-padded matrix. FIG. 11C is a newly registered strip containing the reference strip (outlined by box 1102) and transformed moving strip (outline by box 1104).

FIG. 13A shows the merged image after gross registration. FIG. 13B shows the merged image after fine registration. The regions outlined by boxes 1304 in the images of FIGS. 13A and 13B are shown in enlarged format in FIGS. 13C and 13D, respectively. In FIG. 13C, the large vessels merged after gross registration are not well connected to the single strip region (indicated by arrows), and the small vessels are less clear than that of single strip. In FIG. 13D, the large vessels merged after fine registration are continuous with the single strip and the small vessels are more clear than that of the single strip.

FIG. 15A is a first y-fast en face OCTA image. FIG. 15B is a second y-fast en face OCTA image. FIG. 15C is the merged image after using the disclosed parallel-strip registration method to align the first and second y-fast en face OCTA images. FIGS. 15D, 15E, and 15F show an enlarged view of the regions outlined in the boxes in the images of FIGS. 15A, 15B, and 15C, respectively.

FIG. 16A is a first y-fast en face OCTA image. FIG. 16B is a second y-fast en face OCTA image. FIG. 16C is a merged y-fast en face OCTA image. Note that the arrows in FIGS. 16A and 16B denote lines of missing flow information in the original images which overlap such that, even after merging, flow information is still missing. Performing an interpolation operation of these lines with missing flow operation restores image integrity.

FIG. 17A is a first y-fast en face OCTA image of retina. FIG. 17B is a second y-fast en face OCTA image of retina. FIG. 17C is a merged retinal image using the disclosed parallel-strip registration approach. FIG. 17D is a first y-fast en face OCTA image of the vitreous with retinal neovascularization (RNV). FIG. 17E is a second y-fast en face OCTA image of the vitreous with RNV. FIG. 17F is a merged vitreous image produced by applying the deformable field registration obtained from the retinal slab. The arrow in FIG. 17A indicates a vertical motion artifact crossing through a nonperfusion region.

FIG. 24A is a first en face OCTA. The white vertical line artifacts are caused by microsaccadic bulk motion. FIG. 24B is a second en face OCTA. FIGS. 24C and 24D show the first and second en face OCTA, respectively, after the microsaccadic line artifacts are detected and removed, leaving inter-microsaccadic strips for registration. FIG. 24E shows the merged en face OCTA after affine registration of the strips.

FIG. 25A shows the original reference and moving boundaries. FIG. 25B shows that the transformed moving boundary is translated to match the reference boundary in average height. FIG. 25C shows the average height profile of the reference and transformed moving boundary. FIG. 25D shows the average height profile is smoothed using a moving average filter to obtain the final ILM boundary.

FIG. 26A shows the reference A-line of the normalized reflectance signal. FIG. 26B shows the moving A-line of the normalized reflectance signal. FIG. 26C shows the reference and moving A-line low-pass filtered by the Gaussian function. FIG. 26D shows the moving and reference A-line were registered by minimizing their sum squared difference and shifted to their mean position.

FIG. 27A illustrates the reference B-frame (showing flow signal). FIG. 27B illustrates the moving B-frame. In FIG. 27C, the moving B-frame is overlaid on the reference B-frame without registration. FIG. 27D illustrates the two B-frames after affine registration to minimize sum squared difference. The enlarged regions are outlined.

FIG. 28A illustrates a first volumetric OCT. FIG. 28B illustrates a second volumetric OCT. FIG. 28C illustrates a merged volumetric OCT after the 3D registration of the first and second volumetric OCTs. FIG. 28D illustrates the B-frame along x (slow) axis in the first OCT volume (horizontal line 2802 in FIG. 28J). FIG. 28E illustrates the B-frame along x axis in the second OCT volume (horizontal line 2804 in FIG. 28K). FIG. 28F illustrates the B-frame along x axis in the merged volume (horizontal line 2806 in FIG. 28L). FIG. 28G illustrates the B-frame along y (fast) axis in the first OCT volume (vertical line 2808 in FIG. 28J). FIG. 28H illustrates the B-frame along y axis in second OCT volume (vertical line 2810 in FIG. 28K). FIG. 28I illustrates the B-frame along y axis in the merged volume (vertical line 2812 in FIG. 28L). FIG. 28J illustrates the first en face OCTA. FIG. 28K illustrates the second en face OCTA. FIG. 28L illustrates the merged en face OCTA after 3D registration of the two OCT volumes.

FIG. 30A illustrates a first volumetric OCT. FIG. 30B illustrates a second volumetric OCT. FIG. 30C illustrates a merged volumetric OCT after the 3D registration of the first and second volumetric OCTs. FIG. 30D illustrates the B-frame along x (slow) axis in the first OCT volume (horizontal line 3002 in FIG. 30J). FIG. 30E illustrates the B-frame along x axis in the second OCT volume (horizontal line 3004 in FIG. 30K). FIG. 30F illustrates the B-frame along x axis in the merged volume (horizontal line 3006 in FIG. 30L). FIG. 30G illustrates the B-frame along y (fast) axis in the first OCT volume (vertical line 3008 in FIG. 30J). FIG. 30H illustrates the B-frame along y axis in the second OCT volume (vertical line 3010 in FIG. 30K). FIG. 30I illustrates the B-frame along y axis in the merged volume (vertical line 3012 in FIG. 30L). FIG. 30J illustrates the first en face OCTA. FIG. 30K illustrates the second en face OCTA. FIG. 30L illustrates the merged en face OCTA after 3D registration of the first and second OCT volumes.

DETAILED DESCRIPTION

Figure 1:
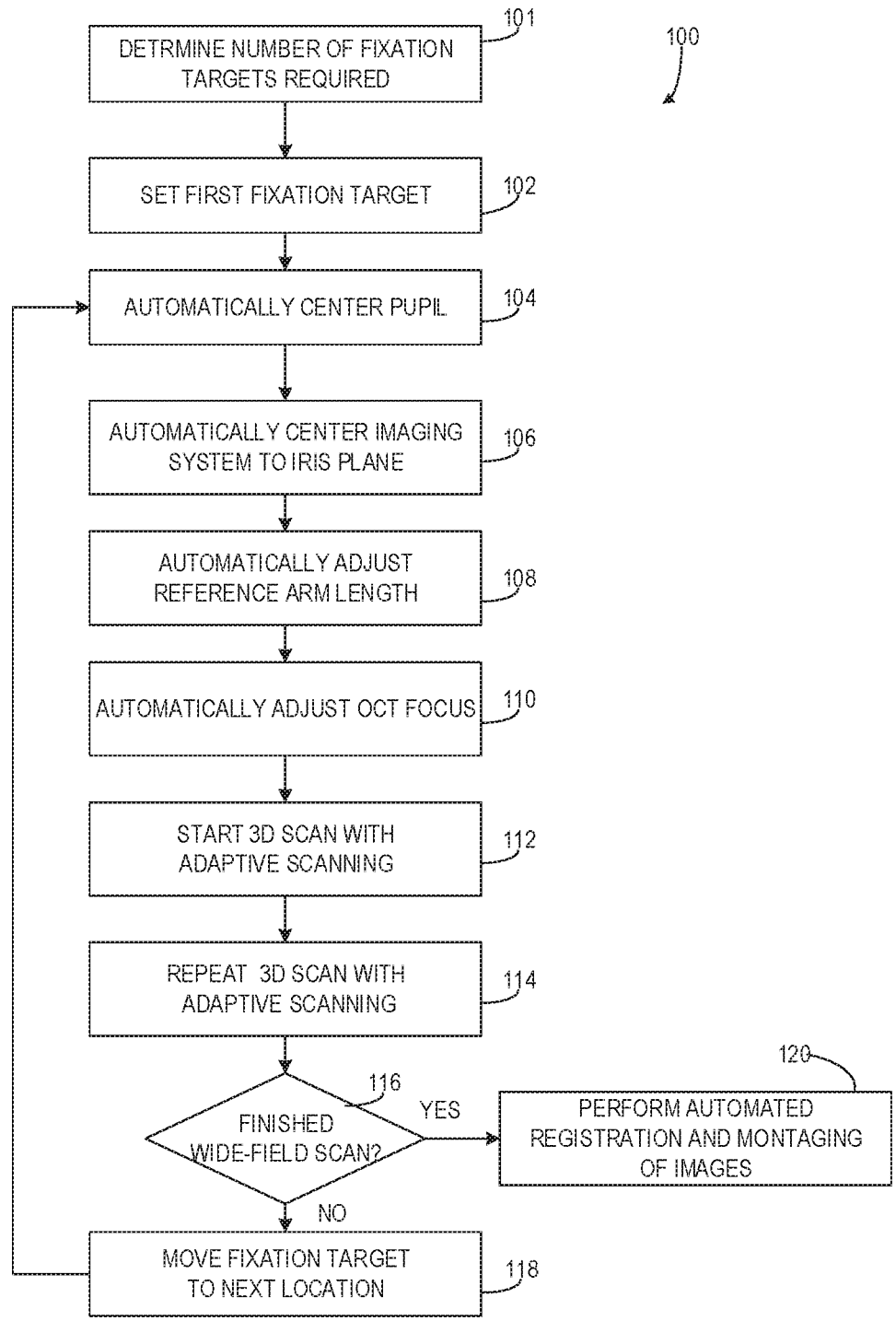
FIG. 1 is a flowchart depicting an example workflow for automatic wide-field OCTA imaging, in accordance with various embodiments.

Disclosed are systems and methods for automatic widefield OCTA imaging that require minimal operator intervention. The disclosed systems and methods allow the acquisition of wide-field OCTA data by montaging (e.g., combining) several motion-free scans acquired at different locations of the retina. The disclosed system includes a tunable fixation target system, an automated system to center the eye pupil, an automated system to center the patient iris plane, an automated system to adjust the OCT reference arm, a fast automated focusing system based on an electrical tunable lens, and an adaptive scanning method for fast response to micro-saccadic eye motion and blinking. In an embodiment, the adaptive scanning method may repetitively acquire B-scans at a given fast-scan location and analyze, e.g., in real time, characteristics of the reflectance intensity images and decorrelation images at that location to determine whether eye blinking or eye motion is occurring. In embodiments, B-scans are repeatedly acquired at said fast-scan location until it is determined that eye blinking and eye motion are no longer detected, whereupon scanning proceeds to the next fast-scan location. The steps for alignment of the patient pupil with the imaging system, adjustment of system optics, 3D scanning and rescanning, and imaging processing are automatically performed by the system. An aspect of the disclosed systems and methods is that they provide a fully automated solution for wide-field OCTA imaging.

A method for automated motion correction using parallel-strip registration and automatic montaging is also disclosed. In embodiments, a plurality of OCTA scans may be acquired and each converted into an en face angiogram format. These angiograms may be corrected to account for variations in reflectance intensity. In some embodiments, the angiograms may further be adjusted to stabilize the mean or median value of decorrelation within the angiogram images, and/or enhanced to boost the contrast and connectivity of the capillary network. The angiograms may then be divided into a plurality of parallel micro-saccade-free strips, wherein artifactual motion lines within a given angiogram are removed to demarcate the division of said angiogram into a plurality of separate strips. In embodiments, strips having maximal overlap are identified and registered to align vascular features within the strips. In embodiments, registration may include a gross registration step wherein large vessels are aligned using a rigid transformation approach. Registration may also include a fine registration step, wherein a non-rigid deformation-based transformation approach is used to align small vessels across overlapping strips. In embodiments, a B-spline free-form deformation algorithm may be used to perform fine registration. An aspect of the parallel-strip-based registration methods described herein is that the strips may be montaged into motion-corrected composite angiogram images. In further embodiments, a set of overlapping motion-corrected composite angiogram images may themselves be montaged (e.g., using the parallel-strip registration method) to automatically generate ultra-wide-field view angiograms using the disclosed methods.

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging based on the detection of spectral interference. Such imaging can be two-dimensional (2-D) or three-dimensional (3-D), depending on the application. Structural imaging can be of an extended depth and width range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is directed along the optical axis (the z-axis) of the OCT device and penetrates the sample being imaged. The A-scan encodes reflectivity information (for example, signal intensity) as a function of depth.

B-scan: A cross-sectional tomograph that may be achieved by laterally combining a series of axial depth scans (i.e., A-scans) in the x-direction or y-direction. A B-scan encodes planar cross-sectional information from the sample and is typically presented as an image. Thus, a B-scan can be referred to as a cross sectional image.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value or a decorrelation value). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A collection of adjacent B-scans can be combined form a 3D volumetric set of voxel data referred to as a 3D image. In the systems and methods described herein, the dataset obtained by an OCT scanning device is termed a "structural OCT" dataset whose values can, for example, be complex numbers carrying intensity and phase information. Such structural OCT datasets can be used to calculate a corresponding dataset termed an "OCT angiography" dataset of, for example, decorrelation values reflecting flow within the imaged sample. There is a correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a projection of the three dimensional dataset onto a single planar image called a 2D en face angiogram. Construction of such an en face angiogram requires the specification of the upper and lower depth extents that enclose the region of interest within the retina OCT scan to be projected onto the angiogram image. These upper and lower depth extents can be specified as the boundaries between different layers of the retina (e.g., the voxels between the inner limiting membrane and outer plexiform layer can be used to generate a 2D en face angiogram of the inner retina). Once generated, the en face angiogram image may be used to quantify various features of the retinal vasculature as described herein. This quantification typically involves the setting of a threshold value or other appropriate discriminator to differentiate, for example, the pixels that represent active vasculature from static tissue within the angiogram. These 2D en face angiograms can be interpreted in a manner similar to traditional angiography techniques such as fluorescein angiography (FA) or indocyanine green (ICG) angiography, and are thus well-suited for clinical use. It is also common to generate 2D en face images from structural OCT data in a manner analogous to that used to generate 2D en face angiograms.

Microsaccades: small, jerk-like, involuntary eye movements that typically occur during prolonged visual fixation. Microsaccades are similar to voluntary saccades but occur over a smaller range of motion.

Optical coherence tomography angiography (OCTA) uses blood flow-induced signal variation as an intrinsic contrast mechanism to differentiate vasculature from static tissues. In an embodiment used for examples herein, OCTA uses repeated B-scans (MB-scan) acquired at one position to assess the variation in OCT signal, or decorrelation, of each pixel. Pixels corresponding to vasculature show fluctuations in the OCT signal due to flowing blood cells while pixels of static tissue show little change. Multiple MB-scans are taken in the slow transverse direction to achieve a volumetric OCTA to represent the vasculature. OCTA images can be presented as 2D en face angiograms to replicate the view of traditional dye-based angiography.

A single OCTA volumetric scan usually takes 3 to 5 seconds, during which involuntary eye movement can introduce motion artifacts to the OCTA images. There are three common types of involuntary eye motions: tremor, microsaccades, and drift (Martinez-Conde S et al, *Nat Rev Neurosci* 5, 229-240 (2004); incorporated by reference herein). Small motions such as eye drift, tremor, or mechanical instabilities of the OCT apparatus can shift the intensity distribution within MB-scans at each position. Consequently, these types of motion result in increased decorrelation signal in otherwise static tissue. These mild line artifacts can be suppressed by subtraction of bulk motion signal and by pre-registration of MB-scans prior to OCTA computation. Large and rapid motions of the eye such as microsaccades introduce motion artifacts that are clearly visible on en face OCTA projections as horizontal or vertical white lines. These large motion artifacts saturate the decorrelation scale and overwhelm flow signal and therefore cannot be corrected by traditional subtraction or registration—these B-frames must be removed. This introduces loss of lines in the en face OCTA images that disrupt the continuity of vascular networks. These lines must be replaced with rescanning or by combining redundant data from multiple scans.

OCTA requires longer imaging times than traditional structural OCT, and any eye motion that occurs during scanning can detrimentally affect the quality of the acquired data. Hardware-based eye tracking approaches can be used to reduce motion artifacts and extend the imaging time needed for OCTA applications. Such eye-tracking approaches are particularly applicable to wide-field OCTA imaging, where susceptibility to motion artifacts is increased. Retinal tracking with scanning laser ophthalmoscope (SLO), for example, is one strategy for detecting microsaccadic motion, pausing the OCTA scanning, and then resuming the scan at the proper location. However, such eye tracking adds complexity and cost to an OCT system, and the slow frame rate of SLO imaging compared OCT B-frame rate introduces inefficiencies.

An alternative approach for reducing motion artifacts is to use software registration algorithms. Software-based methods have the advantage that they do not require modification of system hardware and can thus be adapted for use with commercial OCT instruments. Software-based motion correction has been demonstrated using two orthogonal raster scanned volumes, one scan having horizontal priority (x-fast) and the other having vertical priority (y-fast), wherein an algorithm estimates eye motion, corrects for that motion on an A-scan basis, and then combines the motion-corrected volumes into a single 3D volumetric dataset having increased signal-to-noise ratio. This algorithm may be adopted in an OCT system to register OCTA 3D data by detecting the displacements based solely on 3D structural OCT. The computation of this method is complex because it is performed in 3D. To avoid this complexity, an OCT system may employ an automatic non-rigid registration method by use of two x-fast and two y-fast en face retinal angiograms. This 2D method has been successfully demonstrated on 2.5×2.5 mm OCTA scan. It is, however, limited to mosaicking of 2D datasets.

While the aforementioned orthogonal registration methods are effective in minimizing motion artifacts on the current generation OCT machines running at 70-100 kHz, the requirement for equal sampling density in both transverse dimensions (i.e., the x and y directions) is not well-suited to faster machines having speeds above 200 kHz. Considering that the optimal time delay between B-frame scans is around 3-5 milliseconds (ms) for OCTA of capillary blood flow, the number of A-lines within each B-frame would be higher (600-1000 or higher) than the number of B-frames (<600) that could be accommodated by a comfortable scan time of less than 4 seconds. Therefore, a non-orthogonal scanning and registration scheme would be more efficient.

Disclosed herein are systems and methods for automatic wide-field OCTA imaging. In an embodiment described herein, a system is disclosed which has dedicated software to automatically align an imaging module to optimize the position of the pupil and iris plane. The system is designed to automatically search for an optimized reference arm location and it has a fast automatic focusing module. In embodiments, the fast automatic focusing module can be based on an electrical lens. An adaptive scanning method is used to acquire a motion-free OCTA image to guarantee the image quality during acquisition. Motion artifacts can further be minimized during post-processing of the acquired imaging data, for example, by using a parallel-strip registration algorithm that is disclosed herein. An aspect of the disclosed systems and methods is that the entire acquisition and processing steps for wide-field OCTA imaging can be fully automated, thus offering a solution for wide-field OCTA with minimum human intervention.

FIG. 1 shows a flowchart depicting example steps of a method 100 to be performed by an automated wide-field OCTA imaging system (e.g., imaging system 1900 depicted in FIG. 19) using embodiments of the hardware and software components described herein. The automated wide-field OCTA system (also referred to as the "OCTA system") described herein may be configured, in some embodiments, to follow one or more (e.g., all) of the operations of the method 100 depicted in FIG. 1 to acquire and process images in a sequential manner. Depending on the field of view requested by the user, at 101 the OCTA system determines the number of fixation targets required (e.g., to cover the desired imaging area). In some embodiments, operation 101 may include determining the spatial arrangement of the fixation targets. At 102, the OCTA system may set the first fixation target location. At 104, the OCTA system may automatically center the pupil (e.g., by aligning the chin/forehead rest and patient imaging module). The OCTA system then automatically adjusts the patient imaging module with respect to the iris plane at 106 (e.g., to center the patient imaging module to the iris plane), for example, to optimize OCT scanning of the eye and minimize vignetting. At 108, the OCTA system may automatically adjust the reference arm length of the OCT scanning. At 110, the OCTA system may automatically adjust the OCT focus. At 112, the OCTA system may perform a 3D scan with adaptive motion detection. At 114, the OCTA system may repeat the 3D scan with adaptive motion detection. The 3D scan with adaptive motion detection may be repeated any suitable number of times and may re-scan either a portion of a B-scan line or an entire B-scan line. At 116, the OCTA system may determine whether the full wide-field scan has been completed. If the OCTA system determines that the full wide-field scan had not be completed, then at 118 the fixation point is moved to the next location and the next 3D scan procedure commences at 104 and the OCTA system repeats operations 104, 106, 108, 110, 112, 114, and 116 at the next fixation point location. If it is determined at 116 that the full wide-field scan has been completed, then the OCTA system proceeds to automatic registration and montaging of datasets from different scans at 120 to form a single wide-field, motion-free OCTA image. Further detail for each of the operations of method 100 is provided below.

Tunable Fixation Target Module

In embodiments, a tunable fixation target module is used to set fixation locations according to operations 102 and 118 of FIG. 1. For wide-field OCTA imaging applications as described herein, the tunable fixation target module can be configured to automatically adjust the fixation target location so that imaging of different parts of the retina can be performed sequentially. The images obtained from different parts of the retina can then be montaged or combined during post-processing to create a field of view that is larger than that obtained by a single conventional 3D OCT scan. In embodiments, a video projector or an LCD-based fixation target module can be used to set fixation locations. Such embodiments would allow the user to freely change the location of the fixation target as needed.

Figure 2:
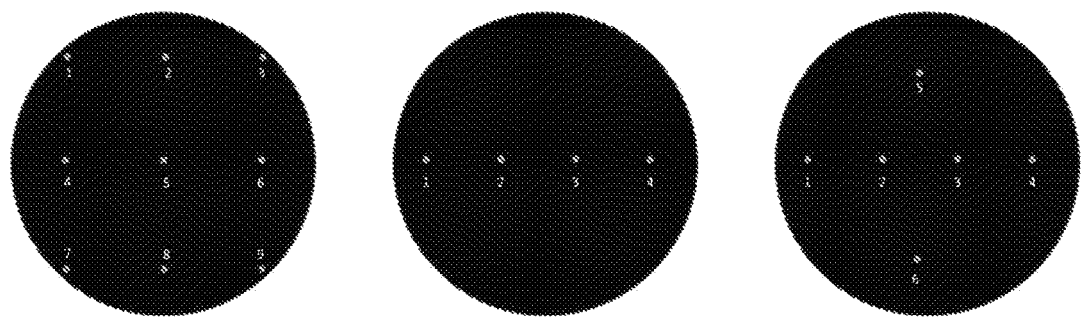
FIG. 2 is a panel of three example fixation target patterns for widefield OCT angiography imaging, in accordance with various embodiments. The leftmost image shows a sequence of fixation targets for montaging 9 scans. The middle image shows a sequence of fixation targets for montaging 4 scans. The rightmost image shows a sequence of fixation targets for montaging 6 scans.

Depending on the size and extent of the field of view to be imaged, different fixation target locations may be needed. In embodiments, once the field of view has been specified, the tunable fixation target module can be configured to sequentially display a series of fixation targets according to a planned imaging sequence. FIG. 2 shows a set of example fixation target locations with numbering schemes to represent the order of acquisition of the corresponding 3D dataset. In the leftmost image of FIG. 2, an example fixation target pattern suitable for acquiring nine (9) overlapping OCT scan datasets is shown. The middle and rightmost images show example fixation target patters for acquiring four (4) and six (6) OCT scan datasets, respectively.

Module for Automatically Centering on Pupil of Eye

In embodiments, each time the fixation target module changes to a new fixation target location, a recording system, for example, a video camera, is engaged to begin monitoring the iris/pupil of the eye. Software and image processing techniques known in the art can be used to automatically detect the center of the pupil based on the images captured by the recording system. The pupil region is typically a dark circle inside a lighter ring (i.e., the iris). Detection of the pupil region may be performed by any suitable technique, for example, using a typical real-time pupil tracking algorithm can be used to detect and track the pupil center. Based on the pupil center detected by the software, the centering module is configured to automatically adjust position of the chin/forehead rest and/or the patient imaging module at 104 to orient the OCT beam with respect to the center of the pupil (e.g., so that the OCT beam enters the eye through the center of the pupil). An advantage of such an approach is that vignetting effects can be minimized for different fixation targets, improving image quality for the whole field of view.

Module for Automatically Centering on the Patient Iris Plane

Figure 3A:
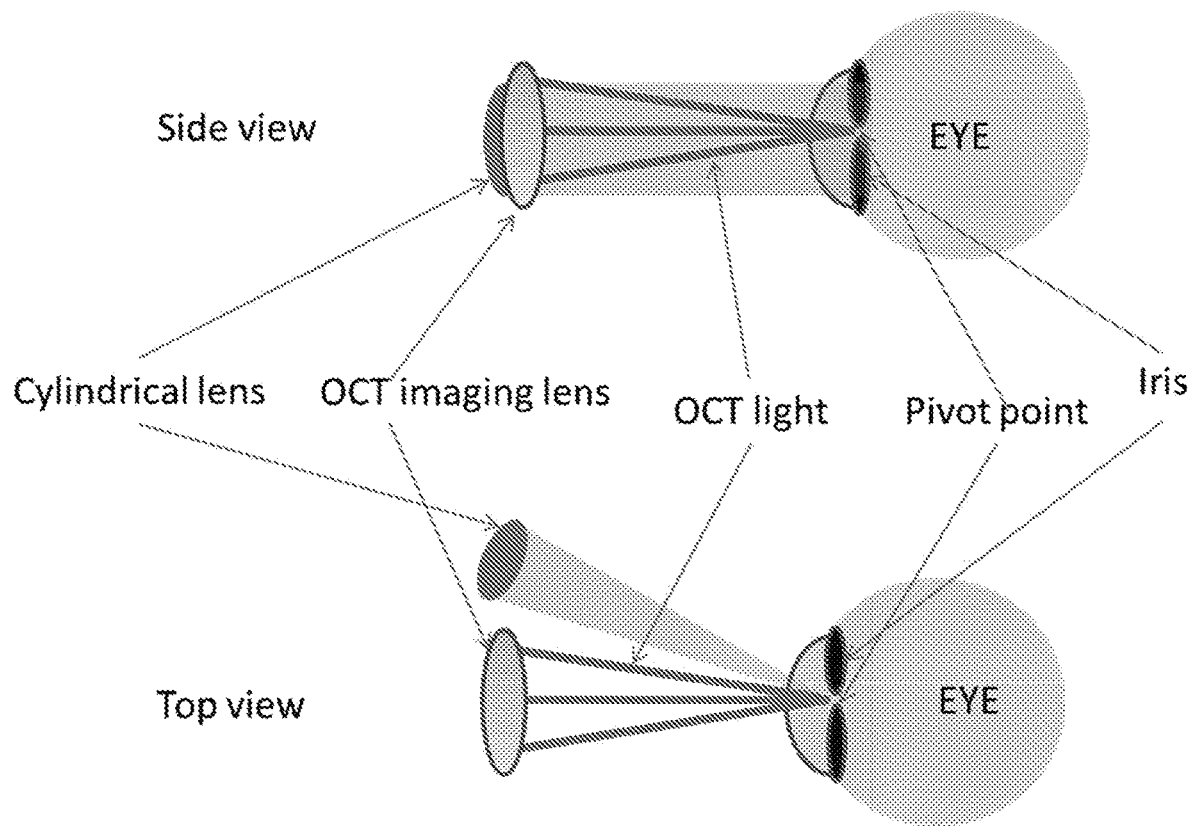
FIG. 3A is a schematic of a side view and a top view of an example layout for a line illumination system for centering the iris plane. A cylindrical lens is used to focus a collimated beam to a line. The focal plane of the cylindrical lens is set to the pivot point plane of the OCT scanner. The line illumination system forms a line on the iris; the line is sharpest when the iris is located at the focal plane of the illumination system.

The distance between the imaging lens and iris plane is an important parameter for wide-field OCT imaging. During OCT imaging when the beam is scanned, it will converge about a pivot point. At that pivot point the size of the pattern formed by the scanned beams is minimized. Vignetting occurs when the OCT imaging beam is blocked by the iris during a portion of the beam scan, resulting in loss of signal over a portion of the OCT image. Thus, in order to minimize vignetting effects, the pivot point of the OCT scanner should be positioned at the pupil of the eye. To realize this pivot point placement, the distance between the iris plane and the imaging lens must be accurately controlled so that the iris plane-to-imaging lens distance is equal to the working distance of the imaging lens of the OCT system. In embodiments this can be achieved by configuring the system to have a line illumination module whose focal plane is set at the pivot point of the OCT scanner as depicted in FIG. 3A. In embodiments, the line illumination module can use colored light, for example, red, green, or other visible wavelengths, as the light source. In an example embodiment shown in FIG. 3B, a line illumination module can be configured to produce vertical line on the iris by passing the LED-generated light through a collimator and then through a cylindrical lens and onto the iris of the eye. A horizontal or other orientation for the line may be produce by appropriate rotation of the cylindrical lens, as will be recognized by those in the art. The image of the line cast onto the iris can be captured by a suitably placed camera. In embodiments, the video camera described above for pupil centering can be used as part of the line illumination module described herein. When the iris plane is aligned with the focal plane of the line illumination module, an image of the line, as recorded by the video camera, will be at its sharpest. Thus, in an embodiment, by monitoring the sharpness of the line on the iris image, it can be determined if the iris plane is located at the focal plane of the line illumination module or at the pivot point of the OCT scanner. In embodiments, this determination can be performed automatically by software. Further, the module can be configured to automatically adjust the distance between the eye and the OCT imaging lens depicted in FIG. 3A in order to acquire a series of video images. These images can be used to calculate the optimum distance between the iris and imaging lens by identifying image and distance combination associated with the sharpest illumination line. In embodiments, the acquisition of these line images over a range of distances and identification of the distance which optimizes line sharpness can be implemented in an open-loop or closed-loop manner with software configured to automatically control an actuator, such as a translation stage, to adjust distance between said imaging lens an the iris plane.

Module for Automatically Adjusting the Reference Arm Path Length

In embodiments, a wide-field OCTA imaging system can also be configured to automatically adjust the reference arm path length to match the retinal location so that the OCT retina image can be shown on a screen, and to calculate the distance between the iris plane and the retina. This adjustment of the reference arm length 108 can be performed, for example, after the pupil is centered 104 and after the iris plane location is centered to the pivot point of OCT scanner 106. In embodiments, the reference arm tuning module can be configured to tune the OCT reference arm length from a minimum path length to a maximum path length at a prescribed step distance, capturing an OCT image after each step. From the series of OCT images obtained at each step, the reference arm tuning module can be programmed to find the optimum reference path length by detecting if there is sample reflection from the OCT image and the location of the sample. In an embodiment, the reference arm path length can be obtained from the location of final reference mirror. The reference arm path length can be used to calculate the distance between iris plane and the retina. In an embodiment, a calibration step using an eye with known distance between iris plane and retina can be used. The eye used for calibration has a distance of L0 between iris plane and retina. The reference path length (in air) is measured to be R0. The reference path length (in air) from the eye under measurement is R1. The distance between the iris plane and retina for the eye under measurement can be calculated by: $L0+(R1-R0)/1.34$.

Module for Automatically Adjusting Focus

In embodiments, a wide-field OCTA imaging system is equipped with automatic focus functionality for high resolution imaging of the retina. In embodiments, mechanically based lens systems can be employed. In other embodiments, tunable lenses can be used. For example, electrical tunable lenses have been used for focal plane optimization and dynamic focus control. In embodiments of a wide-field OCTA system as described herein, an electrical tunable lens (such as from Optotune AG) can be used to optimize the focus plane automatically. In such tunable lens systems, the radius and focal length of the lens can be modulated by changing the control electrical current, and response time is well-suited to live imaging applications (e.g., on the order of milliseconds). Automatic focusing can be achieved by searching the optimized control current by the software. In some embodiments, the optimized control current is found by searching for the current that maximizes the overall image intensity. In some embodiments, automatic focusing can be implemented by a two stage searching scheme comprised of a coarse adjustment of the control current with a large step size to bring the target image into view and fine adjustment of the control current to bring the target image into sharper detail.

Module for Adaptive Motion Detection and Scanning

Figure 4:
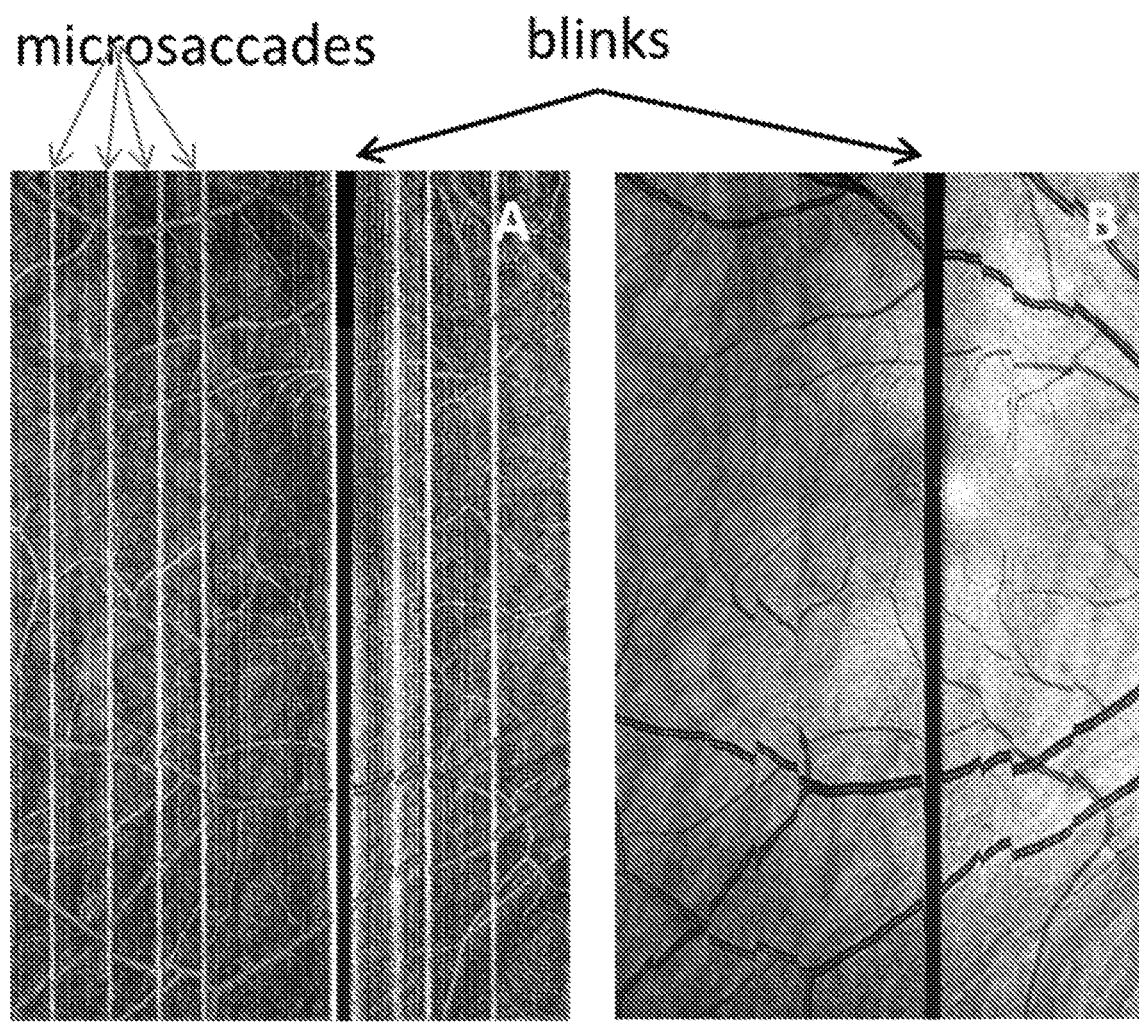
FIG. 4 is a set of en face average intensity projection images from a healthy volunteer subject exhibiting motion-related artifacts, with FIG. 4A being an OCTA image and FIG. 4B being an OCT intensity image. Eye blink events cause a loss of signal which manifests as vertically-oriented black regions in both OCTA and OCT intensity images. Microsacccadic eye movements manifest as bright vertical lines in the OCTA image.

In embodiments, a wide-field OCTA imaging system is equipped with functionality for adaptive motion detection and scanning. This functionality is incorporated to address motion artifacts induced by microsaccades and eye blinking. As shown in FIG. 4, microsaccades manifest as bright lines in OCTA images, while eye blink events cause a temporary loss of OCT signal, and thus manifest as black lines in both OCT intensity and OCTA images. These bright and dark lines can be either vertical or horizontal, depending on scanning priority of the laser raster.

Figure 5:
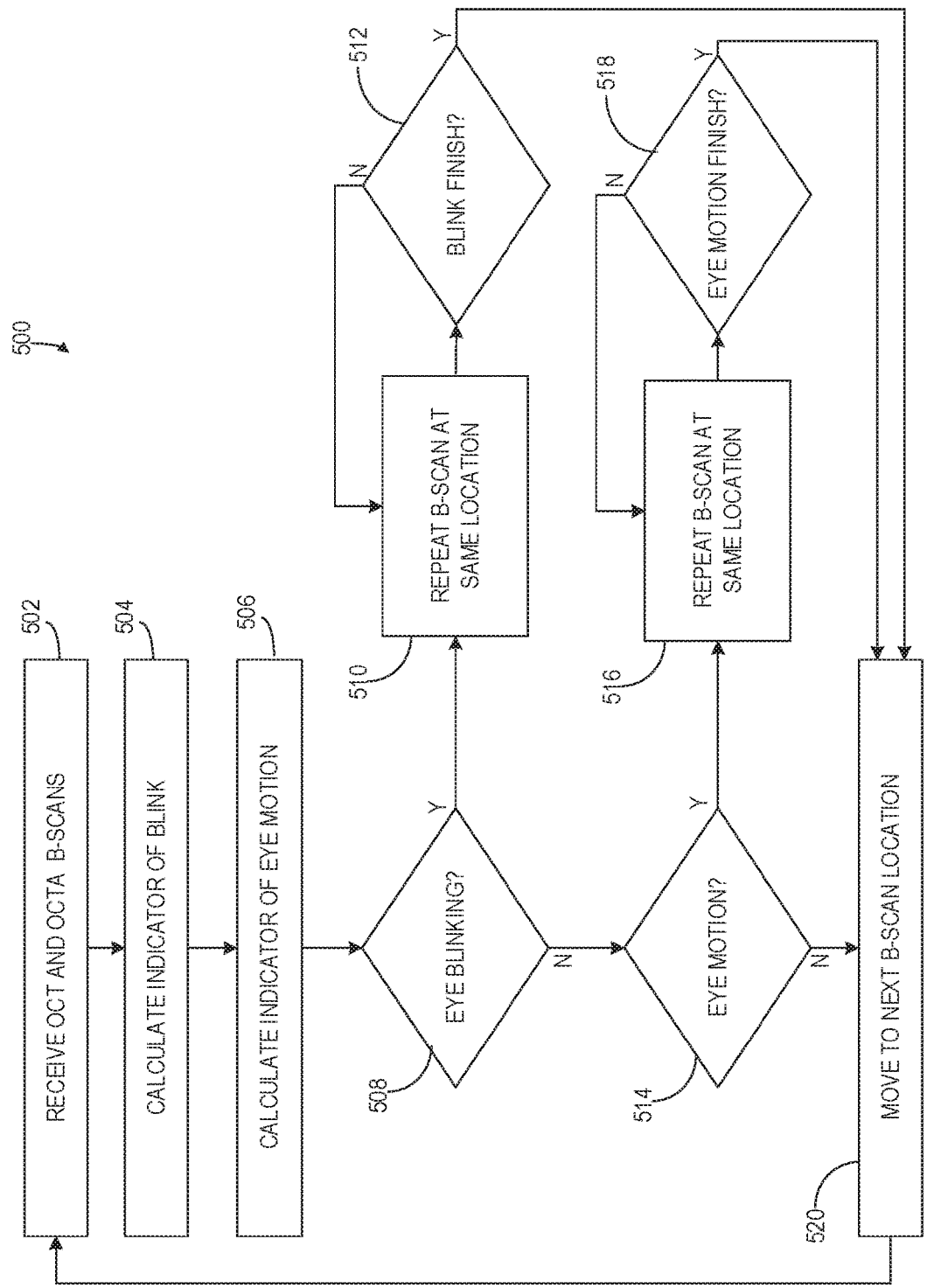
FIG. 5 is a flow chart for an example adaptive rescanning procedure.
Figure 6A:
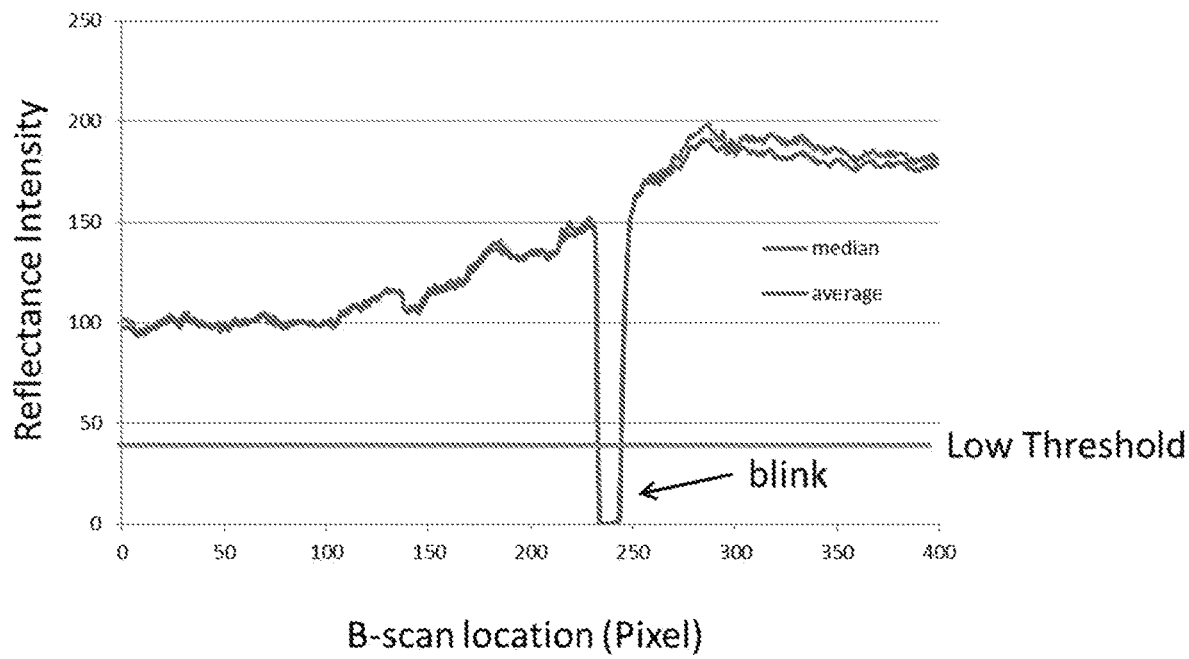
FIG. 6A is a graph showing the signal variation in a set of OCT B-scan images comprising a volumetric OCT scan. Median and average intensity values for each B-scan OCT intensity image are shown. An eye blink event for a B-scan is characterized by loss of the reflectance intensity signal, such that a low threshold can be established to identify B-scans associated with eye blinking.

In an embodiment of an adaptive motion detection and scanning method, cross-sectional OCT intensity and OCTA images are used to detect eye motion and provide feedback for rescanning. FIG. 5 shows a flow chart for an example adaptive rescanning technique wherein the wide-field OCTA system automatically detects microsaccadic and blink events. Blink events are detected during the acquisition of each B-scan OCT intensity image as the loss of OCT intensity signal (see FIG. 6A). Once a blink event is detected, the system maintains the scanning at the same position (i.e., the same slow scan elevation) and continuously scans and monitors to determine when the blink has ended (i.e., the OCT intensity signal has been restored). In embodiments, this detection and monitoring can be realized by continuously calculating a quantity that characterizes the B-scan image and distinguishes blink events from normal scans captured during image acquisition. In embodiments, this detection and monitoring can be realized by calculating, for example, the mean or median value of the intensity of each B-scan image and comparing that value to a specified threshold. In an alternative embodiment, detection of a blink event for a given B-scan can be performed by counting the number of pixels with intensity values above or below a specified threshold (FIG. 6A). In embodiments, the blink event calculation and threshold comparison can be performed each time a B-scan is acquired such that incrementing of the slow-scanning position can be interrupted when a blink event is detected. During such an interruption, the system can be configured to continuously scan at the fixed slow-scan position until the blink event calculation indicates a normal scan has been acquired. Once the eye blinking event has concluded, the system will, in an embodiment, re-position the galvanometer mirror and rescan from the location where the initial blink is detected. In embodiments, the system can also be configured to begin re-scanning at a specified slow-scan increment prior to detection of the blink event.

Figure 6B:
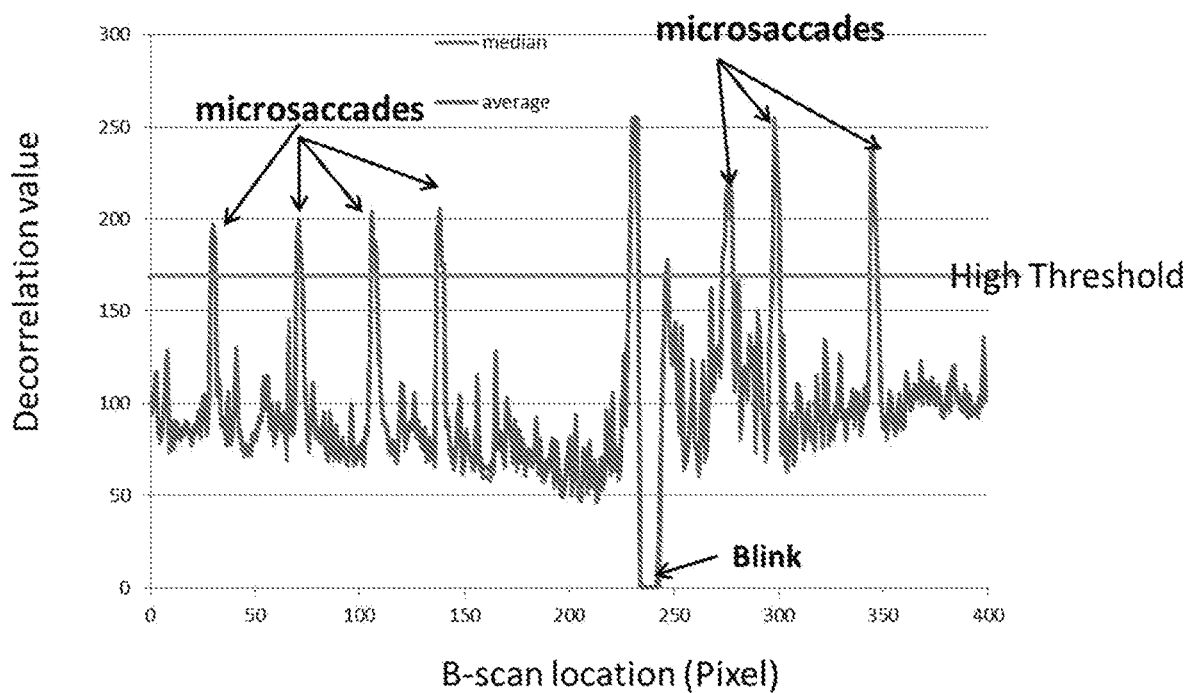
FIG. 6B is a graph showing the signal variation in a set of OCTA B-scan images comprising a volumetric OCTA scan. Median and average decorrelation values for each B-scan OCTA image are shown. Both eye blink and micro-saccadic events can be detected in the OCTA B-scans images. As shown, eye blink events are characterized by loss of the decorrelation signal, while micro-saccades are characterized by high decorrelation values. Thus, a high threshold for the decorrelation value can be established to identify B-scans associated with micro-saccadic eye movement.

In embodiments, microsaccadic eye movements can also be detected during scanning as part of an adaptive motion detection and scanning method. Provided that blinking is not detected during a scan (for example, as described above using the OCT intensity images), the system can further perform an automatic query for the presence of eye motion. As noted previously, OCTA images exhibit distinct artifacts associated with microsaccadic motion. As shown in FIG. 6B, the distributions of the decorrelation values in the tissue region for OCTA with eye motion and OCTA without eye motion are very different. For example, the OCTA decorrelation values with eye motion have a higher mean and median value than OCTA without eye motion. Thus, in an embodiment, specification of a median or mean decorrelation threshold value can be used to the detect eye motion in tissue region, similar to the method used for blink detection.

From a system performance and implementation standpoint, detection of eye motion artifacts during adaptive scanning does not require the use of high resolution OCTA images, as might be produced by the split-spectrum amplitude decorrelation angiography algorithm. Thus, in embodiments, it is advantageous to implement a lower resolution and less computationally intensive flow detection algorithm for the adaptive motion detection and scanning component of the wide-field OCTA imaging system in order to improve system performance. In embodiments, a less computationally intensive method can include direct subtraction of two OCT intensity images from two repeated B-scans. Other embodiments can include a reduced-spectrum method, wherein only a portion of the spectrum is used for motion detection to speed the calculation. For example, in an embodiment, a four-fold reduction of the spectrum pixel has been observed to reduce processing time by approximately 3.5-fold. It is to be understood that implementation of lower resolution methods to adaptively detect motion in OCTA images during scanning does not preclude the additional implementation of higher-resolution OCTA methods in the system for purposes such as image presentation and data analysis.

In embodiments of an adaptive motion detection and scanning method, once eye motion is detected, the system is programmed interrupt the progress of the slow scan axis galvanometer mirror, maintaining it at its current position, and repeat B-scans along the fast-scan axis until it is determined that eye motion has subsided (FIG. 5). After the eye motion is deemed stabilized, the system advances the scanner to next B-scan location and continues the 3D scanning process.

Method for Image Registration and Image Montaging

In embodiments, a wide-field OCTA imaging system is equipped with functionality to remove motion artifacts and register images as part of a post-processing procedure. Disclosed herein is a method to remove motion artifacts using parallel strip registration and to merge two or more en face angiograms in the same transverse priority. A gross registration based on large vessels is used to correct transverse motion, and a fine registration based on small vessels is used to correct discrepancies between two angiograms caused by drift and image warping. The same registration algorithms can be utilized to montage multiple en face angiograms into an ultrawide-field view.

Figure 7:
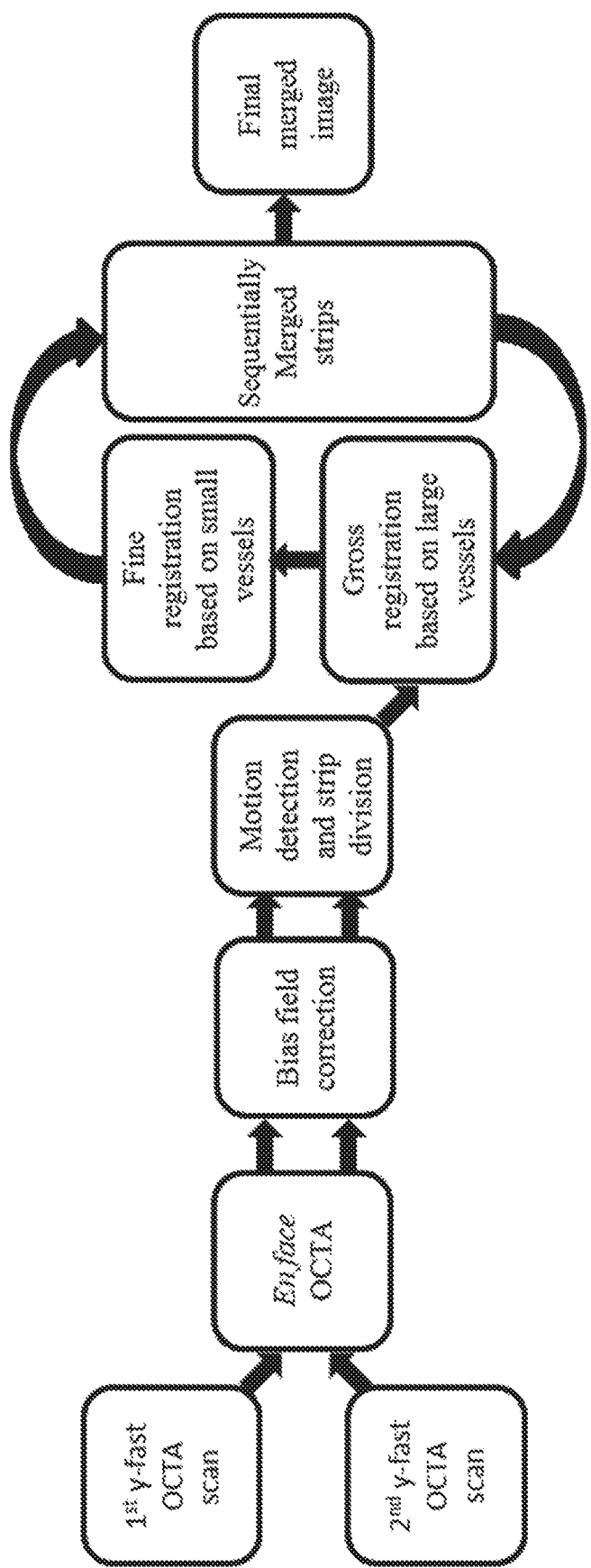
FIG. 7 is a flow chart of an example automated motion correction algorithm.

Parallel-strip registration scheme: Two types of motion artifacts affect en face OCTA: one that can be corrected by translation of one or more successive B-frames rigidly, and another that can be corrected only by non-rigid deformation within a certain region. To register two scans within the same transverse priority, in an embodiment, each en face angiogram can be divided into parallel microsaccade-free strips. First, the rigid alignment based on large vessels is performed to correct large transverse motion. This rigid alignment procedure is termed "gross registration." Next, a non-rigid alignment based on small vessels (capillaries) is applied to correct small deformation. This non-rigid alignment is termed "fine registration." The flowchart of FIG. 7 summarizes an example implementation of the parallel-strip registration scheme described herein.

Figure 8:
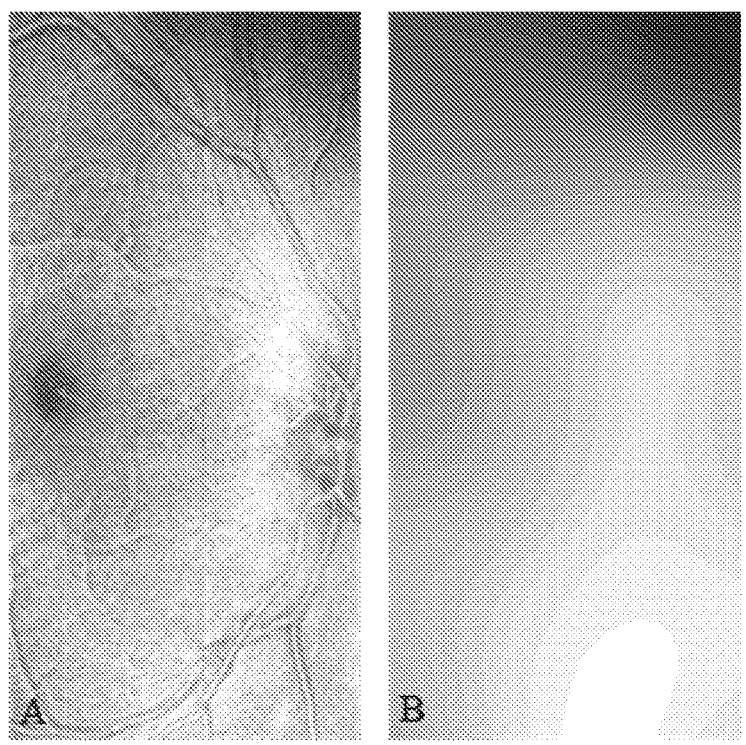
FIGS. 8A-8B are a set of images showing an example of a bias field calculated from an OCT reflectance image.

Bias field correction: The OCT reflectance signal is relatively low in regions where the retina is out of focus (for example FIG. 8A, top-right corner). The decorrelation signal (D), which is calculated from the OCT reflectance signal (S), is also reduced in those regions. To correct this dependence, an illumination bias field (FIG. 8B) can be created. In embodiments, this illumination bias field can be created, for example, by applying a low pass, blurring, smoothing, or other similar filter to the en face reflectance image of retina. For example, an X×Y pixel Gaussian filter with 100 pixel standard deviation applied to the en face reflectance image of FIG. 8A results in the bias field shown in FIG. 8B. The corresponding en face angiogram can then be then corrected using the bias field, for example, using the following formula (Equation (1)):

$$D'(x, y) = D(x, y) * \frac{\text{Mean}(G(S))}{G(S(x, y))} \quad (1)$$

$$(x = 1, 2, 3, \ldots, X; y = 1, 2, 3, \ldots, Y)$$

where X×Y is the size of the en face angiogram, Mean (G(S)) is the mean value of the bias field, D(x,y) is the en face angiogram and G(S(x,y)) is the bias field by filtering en face reflectance image.

Figure 9:
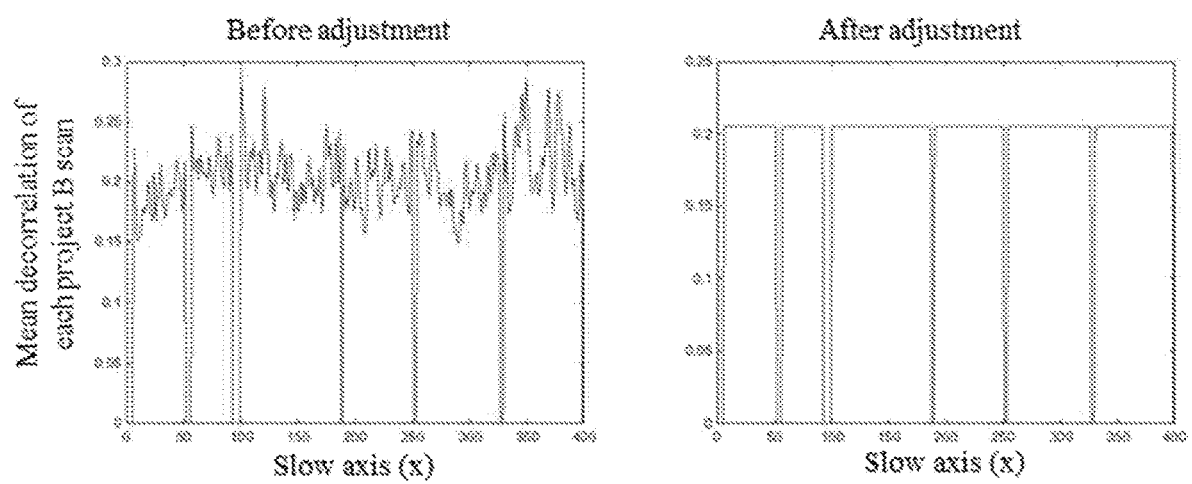
FIG. 9 is a set of two graphs showing plots of mean decorrelation values of projected OCTA B-scans before adjustment (left) and after adjustment (right) to correct for motion artifacts. As shown in the right graph, lines with large eye movements have been removed, resulting in decorrelation values of zero. In addition, decorrelation values in each line are adjusted so that their mean values remain stable.

Motion detection and strip division: An example of large eye movements manifesting as white lines in OCTA is shown in FIG. 9A. The decorrelation signals of these lines are generally saturated and do not contain useful blood flow information. Also, the scanned regions on either side of the motion artifact region are usually misaligned. These large motion artifacts were detected and removed as lines (projected B-scans) with mean decorrelation value larger than 1.5 times the mean decorrelation value of the entire en face image (FIG. 9B).

Figure 10:
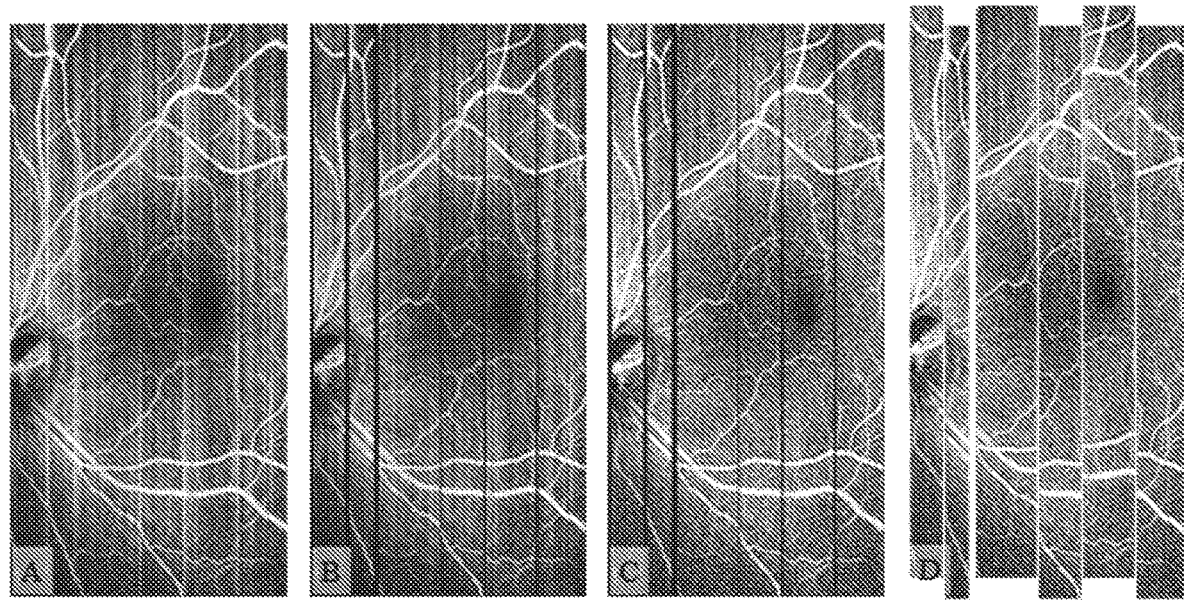
FIGS. 10A-10D are a set of images showing an example motion detection and strip division process applied to an en face OCTA image.

Small eye movements such as tremor cause incompletely saturated decorrelation variation among B-scans (FIG. 10B). To correct this, in an embodiment, the decorrelation values in each line can be adjusted so that their mean values remain stable (FIG. 9B). In addition, local histogram equalization can be applied to boost the contrast of capillary vascular network. In an embodiment, application of histogram equalization with a 5×5 pixel grid to the whole en face image has been found to provide improved contrast of capillary vascular network. Further, vessel connectivity and structure can be enhanced by application of appropriate algorithms or filters. Examples of such filters include the Gabor filter (Estrada R et al, *Biomed Opt Express* 2, 2871-2887 (2011); incorporated by reference herein), Frangi filter (Frangi A et al, *Medical Image Computing and Computer Assisted Intervention—MICCAI'98* 130-137 (1998); incorporated by reference herein), and anisotropic Markov random field-based approaches (Grau V, et al, *IEEE Trans Med Imaging* 25, 245-255 (2006); incorporated by reference herein). FIG. 10C shows an example of enhancement by application of histogram equalization and use of a Gabor filter. The en face image can then be divided into microsaccade-free strips at the detected motion lines (FIG. 10D).

Gross registration based on large vessels: After the microsaccade-free parallel strips are obtained, a gross registration of en face OCTA can be performed based on large vessels to correct the malposition among strips. In embodiments, large vessels can be recognized as pixels with a decorrelation value greater than a specified threshold, for example, 1.3 times the mean value of the corresponding strip (colored in yellow in FIGS. 11A and 11B). In embodiments, a similarity registration can be used to account for translation, rotation, and focusing differences between en face strips. For example, a registration process utilizing a gradient descent to search for a similarity transformation that minimizes the squared difference of the large vessels of two zero-padded strips can be employed.

Figure 11:
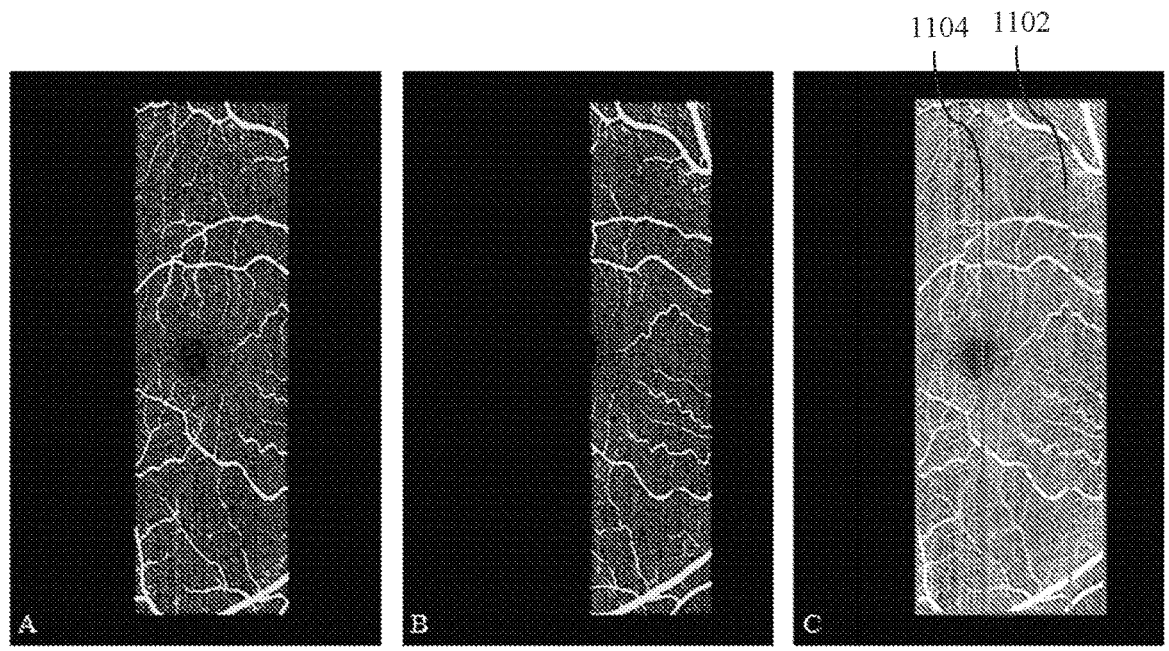
FIGS. 11A-11C are a set of images showing an example of gross registration of two micro-saccade-free parallel strips based on large vessels. The large vessels are shown in yellow and small vessels are shown in purple.

A specific embodiment of gross registration based on large vessels is as follows. All strips are zero padded to 100 pixels wider and higher than the original en face image. Then, any two strips (one from each volumetric scan) containing the largest overlap are considered as the reference strip and the moving strip. Here, large vessels are termed reference large vessel $L_r$ (x, y) and moving large vessel $L_m$ (x, y). The goal is to then find a transformation:

$$T_l(x, y; t) = \begin{pmatrix} t_1 & t_2 \\ t_3 & t_4 \end{pmatrix} \begin{pmatrix} x \\ y \end{pmatrix} + \begin{pmatrix} t_5 \\ t_6 \end{pmatrix} \quad (2)$$

of the moving strip that minimizes the squared difference of the reference large vessel and transformed moving large vessel:

$$C_l(t) = \sum_{x,y} [L_r(x, y) - L_m(T_l(x, y; t))]^2 \quad (3)$$

where (x, y) is the pixel coordinate and t is a vector of transformation parameters. This minimization can be solved iteratively by:

$$t^{(k+1)} = t^{(k)} + \alpha d^{(k)} \quad (4)$$

$$d^{(k)} = -\frac{\partial C_l^{(k)}}{\partial t}$$

where $\alpha$ is the iterative step size, and $d^{(k)}$ is the gradient descent. FIG. 11 shows an example of the gross registration (FIG. 10C) between reference strip (FIG. 11A) and transformed moving strip (FIG. 11B). The gross registration is followed by the fine registration described below.

Fine registration based on small vessels: Slow eye motions within strips, such as those induced by eye drift, cause small scale distortions. These artifacts can be corrected by aligning the small vessels with a deformable registration of the overlapped area. In an embodiment, a multiscale vessel enhancement filter is first applied to enhance the capillary network. Next, pixels that were not previously identified as large vessels, but have decorrelation values greater than a specified threshold, for example, 0.6 times the mean value of the entire corresponding strip, are defined as small vessels ($S_r$ and $S_m$ in reference and moving strips, respectively). Then the fine registration is performed using a deformable registration algorithm such as optical flow or diffusion-based methods, B-spline deformation methods, thin plate spline methods, and elastic registration-based methods. An implementation of a deformable registration algorithm based on the B-spline Free-form deformation (FFD) algorithm is described below.

The size of the mesh grid is specified as $n_x \times n_y$ and the control points $\phi_{i,j}$ are defined as the vertices of each grid. The local deformable field function can be written as:

$$T_s(x, y) = \sum_{p=0}^{3} \sum_{q=0}^{3} B_p(u) B_q(v) \phi_{i+p, j+q} \quad (5)$$

where $i = \lfloor x/n_x \rfloor - 1$, $j = \lfloor y/n_y \rfloor - 1$, $u = x/n_x - \lfloor x/n_x \rfloor$, $v = y/n_y - \lfloor y/n_y \rfloor$ and $B_p$, $B_q$ represents the p or q-th basis function of the B-spline.

$$B_0(u) = (1-u)^3/6$$

$$B_1(u) = (3u^3 - 6u^2 + 4)/6$$

$$B_2(u) = (-3u^3 + 3u^2 + 3u + 1)/6$$

$$B_3(u) = u^3/6 \quad (6)$$

Figure 12:
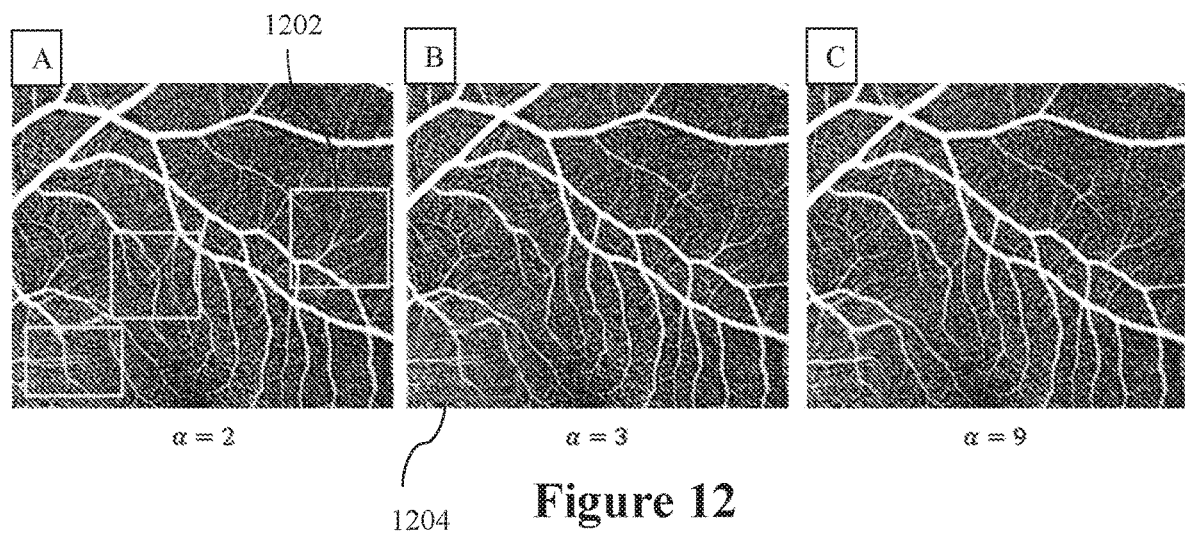
FIGS. 12A-12C are a set of images showing a comparison of merged images registered using different weighting values (a) between large and small vessels. The region size is 6 mm×5 mm in this example. For FIG. 12A, with α=2, the merged image shows incorrectly registered vasculatures indicated by boxes 1202. For FIG. 12B, with α=3, the merged image is improved, but a double vessel still remains, outlined in box 1204. For FIG. 12C, with α=9, the registration is optimized and merged image shows the best quality.

The B-splines are locally controlled, so that each control point only affects limited points in the neighborhood. Each pixel is calculated according the transformed control points. The $T_s(x, y)$ is found by a gradient descent method with two weighting cost functions $C_{smooth}$ and $C_{similarity}$.

$$C_{smooth} = \frac{1}{A_o} \int\int_{(x,y)\in A_o} \left[ \left(\frac{\partial^2 T_s}{\partial x^2}\right)^2 + \left(\frac{\partial^2 T_s}{\partial y^2}\right)^2 + \left(\frac{\partial^2 T_s}{\partial xy}\right)^2 \right] dxdy \quad (7)$$

$$C_{similarity} = \frac{1}{A_o} \int\int_{(x,y)\in A_o} (S_r - S_m(T_s[T_l(x, y)]))^2 dxdy \quad (8)$$

where $A_o$ is the area of overlap. Considering the large vessels carry much larger flow than small vessels, their cost functions are handled separately:

$$C_{fine} = \alpha \cdot (\lambda \cdot CL_{smooth} + CL_{similarity}) + \lambda \cdot CS_{smooth} + CS_{similarity} \quad (9)$$

where CL and CS are the cost functions for large vessels and small vessels, respectively. $\lambda=0.01$ was chosen based on the magnitude of $C_{smooth}$ and $C_{similarity}$, and $\alpha$ was the weighting value between large vessels and small vessels. In the implementation described herein, $\alpha=9$ was chosen based on a test using pilot data sets. FIG. 12 shows a comparison of registration results using different weighting values for $\alpha$.

After the optimal transformation is found by an iterative gradient descent technique, the overlapped region of grossly registered moving strip M(x,y) is transformed by the deformable field just obtained.

$$M'(x',y') = M(T_s(x,y)) \quad (10)$$

Figure 13:
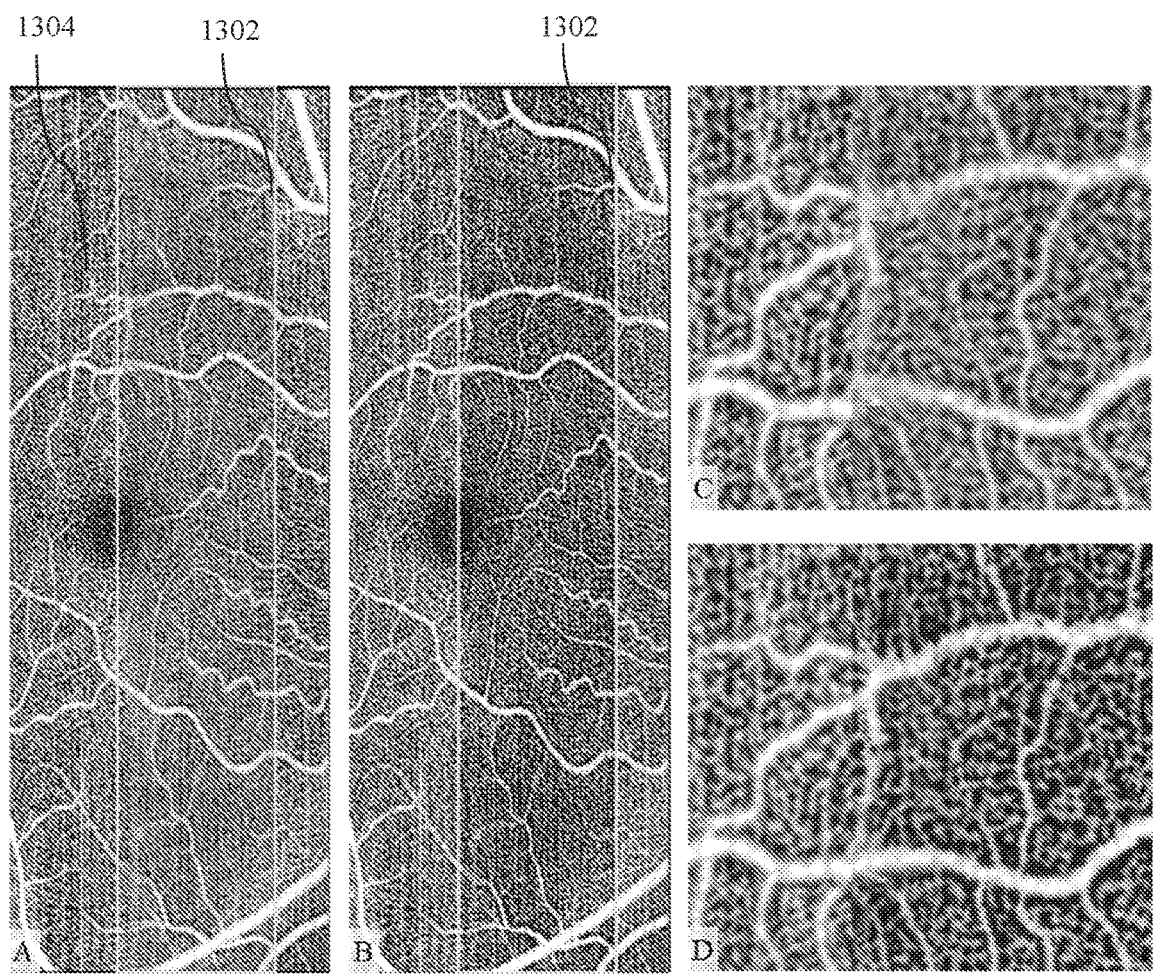
FIGS. 13A-13D are a set of images showing a comparison of a region (outlined in boxes 1302) merged after gross registration and fine registration of two strips.

The completeness, veracity, and distinguishing degree of vasculature in the overlapped region is improved in the final merged image by registering the reference region R(x, y) and the transformed region M'(x', y') together. FIG. 13 shows an example comparison of merged OCTA images with and without fine registration.

The merged strip after both gross and fine registration process is considered as the new reference strip. Next, a new moving strip containing the largest overlap with the new reference strip is registered. This process is repeated until all strips are registered into one comprehensive en face OCTA image.

Montage of adjacent wide field images: The method described above can be applied for the automatic montaging of wide-field OCTA en face images acquired at a known region of the eye containing an overlap of consistent vascular patterns. For instance, in the Example 1 study described below, a 23×10 mm montage was generated using five OCTA scans with each scan covering an area of 6×10 mm. The five scans were acquired sequentially at peripapillary, macular, temporal perifoveal, and temporal peripheral fields by changing the fixation target. This acquisition pattern allowed adjacent scans to have small areas of overlap, approximately 1.5×10 mm. Each scan was considered to be a separate "strip" during the montaging registration procedure.

The techniques described above are effective to correct for microsaccades and other motion artifacts in en face angiograms, but may not be suitable to correct motion on volumetric data, and the distortion of angiographic and structural B-frames on the slow-axis cannot be removed. Correction of motion artifacts on the volumetric data not only provides clinically useful cross-sectional images along slow-axis, but also improves the segmentation efficiency on retinal layers. In addition, a motion-corrected OCT volume can improve volume rendering of the retinal vasculature, the optic disc, and the fovea.

One technique for motion correction on OCT volume is a 3D orthogonal method in which the information in x-fast and y-fast volumetric raster scans and registered A-scans are individually combined by finding a 3D motion field that minimizes an energy function. This algorithm may be used to register angiographic and structural OCT data by detecting the motions calculated from 3D structural OCT. Although this technology greatly improves the merged scan quality, residual lines can still persist on OCTA.

Accordingly, various embodiments herein provide a new 3D registration algorithm for OCT volume based on both angiographic and structural OCT information. The vasculature on en face retinal OCTA is used for transverse registration and the inner limiting membrane (ILM) boundary on structural OCT is taken as the reference for axial registration. Building on the techniques described herein with respect to parallel registration suitable for the ultrahigh-speed OCT (above 200 kHz), this 3D registration algorithm will provide a comprehensive registration system for automated volume rebuilding in wide-field angiographic and structural OCT. Further description of the 3D registration algorithm is provided below with respect to Example 4.

EXAMPLES

Example 1

A registration method to correct motion artifacts for wide-field optical coherence tomography angiography (OCTA) acquired by ultrahigh-speed swept-source OCT (>200 kHz A-scan rate) is demonstrated. Because the number of A-scans along the fast axis is much higher than the number of positions along slow axis in the wide-field OCTA scan, the registration scheme is applicable to non-orthogonal datasets. In the implementation presented herein, two en face angiograms in the vertical priority (2 y-fast) are divided into microsaccade-free parallel strips. A gross registration based on large vessels and a fine registration based on small vessels are sequentially applied to register parallel strips into a composite image. This technique is extended to automatically montage individual registered, motion-free angiograms into an ultrawide-field view.

Study population: the study described herein was conducted at the Casey Eye Institute at the Oregon Health & Science University. The study adhered to the tenets of the Declaration of Helsinki and was approved by the Institutional Review Board. Five healthy participants (age, 30±5) and two participants with proliferative diabetic retinopathy (PDR) (age, 32 and 67) were recruited to the study.

Image acquisition: a prototype OCT system with an axial scan speed of 200 kHz using a swept-source cavity laser (Axsun Technologies Inc., Billerica, Mass.) operating at a center wavelength of 1045 nm with a tuning range of 100 nm was used. A dual-balanced detector (PDB471C, Thorlabs Inc) converted the optical signal to an electrical signal, and a high speed digitizer (ATS 9360, Alazar Technologies Inc., Pointe-Claire, QC) acquired the electrical signal. A resolution of 7.5 µm axially and 12 µm laterally with an imaging depth of 7 mm was achieved. The light power exposure at the cornea was 1.4 mW, which is within the American National Standards Institute safety limit.

Two 6×10×7 (x×y×z) mm volumetric y-fast scans were captured at the same region of posterior pole of each eye. Five different regions were scanned on each eye. In each volumetric scan, the beam was scanned 10 mm vertically to form a B-frame. Each B-frame consisted of 850 axial lines. At each position, 2 consecutive B-frames (MB-scan) were captured in order to detect motion induced signal variation. The MB-scan was then shifted slightly to a new position along the slow (vertical) axis. A total 400 slow-axis locations were sampled to form a 3D OCTA volume. This yielded a lateral sampling density of 11.4 µm along the fast transverse scan axis and 15.0 µm in the slow axis. One volumetric scan was acquired in approximately 4 seconds.

Figure 14:
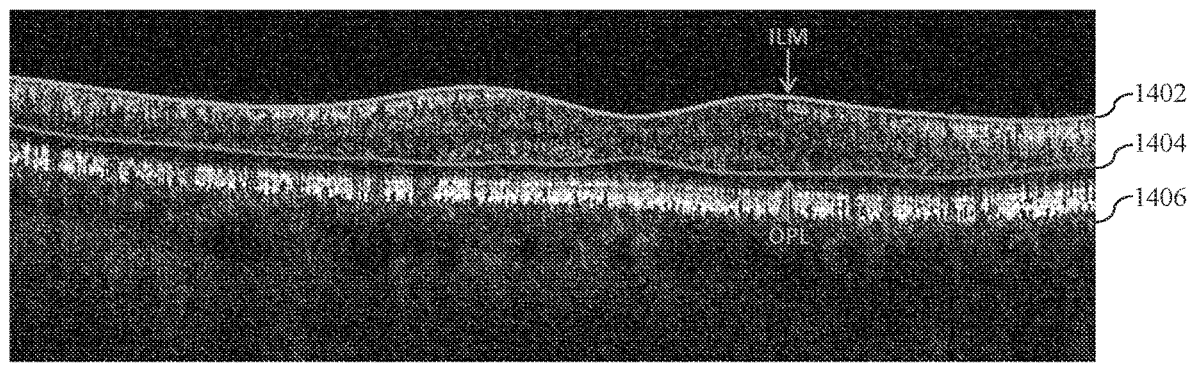
FIG. 14 is a cross sectional image showing a segmentation of the inner limiting membrane (ILM, marked by line 1402) and outer plexiform layer (OPL, marked by line 1404) on one y-fast B-frame from a healthy eye. En face images were generated from the mean value of the region between the ILM and OPL. Decorrelation signal 1406 is shown.

The split-spectrum amplitude-decorrelation angiography (SSADA) algorithm was used to acquire blood flow information between two consecutive B-frames of the same location (Jia Y et al, 2012 supra). The volume data was segmented along the inner limiting membrane (ILM) and outer plexiform layer (OPL). Mean projection of reflectance and maximum projection of decorrelation were used to generate en face views within a slab between the ILM and OPL (FIG. 14).

Results: the automated parallel-strip registration between two strips took an average 11.8 seconds and within that time, the preprocessing steps (bias field correction and motion detection & strip division) took about 5.9 seconds. The test was performed on a workstation with Intel(R) Xeon(R) CPU E3-1226 v3 @ 3.30 GHz and 16.0 GB RAM using MATLAB 2014b (Mathworks, Natick, Mass.).

Figure 15:
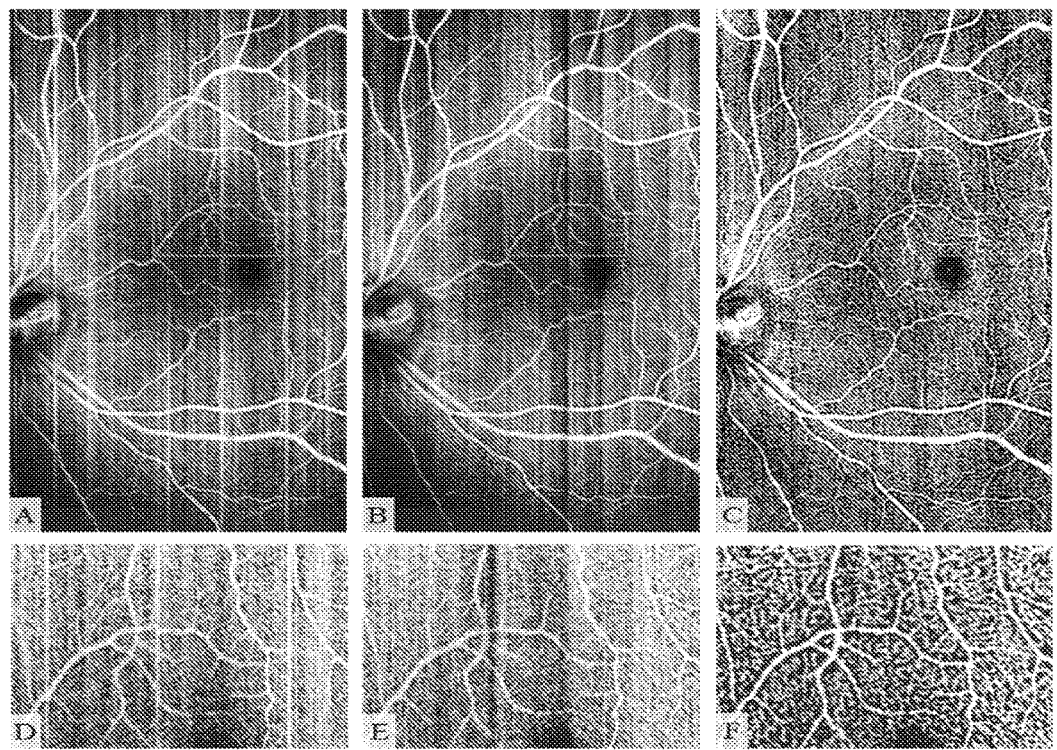
FIGS. 15A-15F are a set of images demonstrating the removal of artifacts using parallel-strip registration applied to two y-fast en face OCTA images of a healthy retina. The size of the imaged region is 6 mm×10 mm.

FIG. 15 shows en face OCTA images of a healthy retina before and after applying parallel-strip registration method to y-fast scans (FIGS. 15A-B, D-E). Large transverse motion artifacts and incoherence of vasculature were corrected in the merged image (FIGS. 15C, F). On FIGS. 15A and 15B, it can be observed that the flow signal at the lower and upper left corners of en face image is poor, resulting in the capillaries having low contrast. These defects have been corrected (FIG. 15C) using the disclosed method. Retinal capillary networks which were affected by motion artifacts in the original y-fast en face OCTAs can be easily identified in the merged image (FIGS. 15C and 15F). Also, the background has been suppressed while flow signals have been enhanced.

Figure 16:
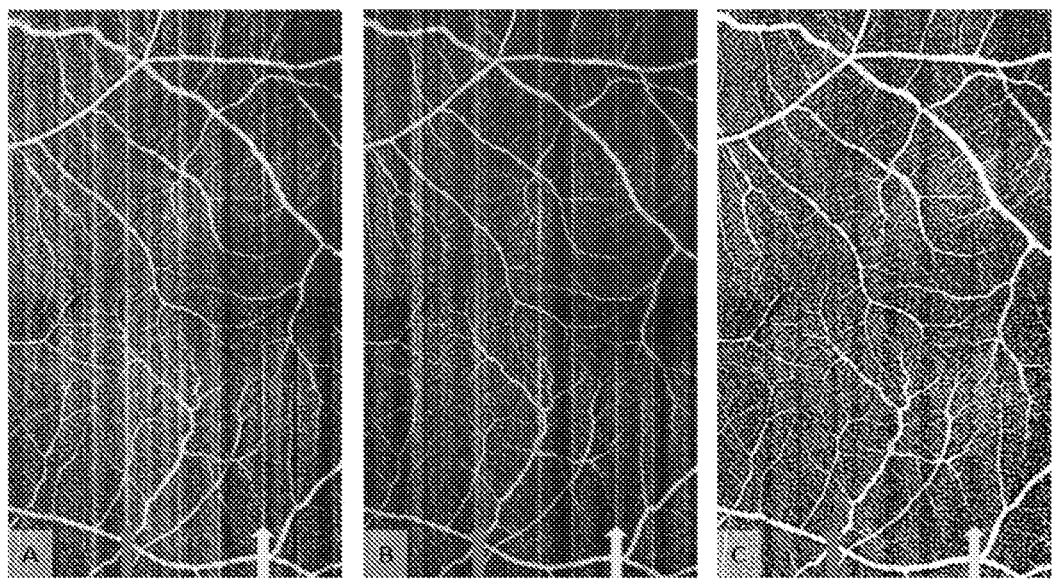
FIGS. 16A-16C are a set of images showing the use of interpolation in conjunction with the merging procedure to restore information at sites where microsaccade motion artifacts overlap in y-fast scans images.

By visual inspection, motion artifacts were reduced in all merged wide-field en face angiograms after parallel-strip registration compared to unregistered y-fast scans. To quantitatively evaluate the capability to remove microsaccadic motions, the number of microsaccade motion artifacts (white lines) present in original en face y-fast OCTA were counted, as well as the number of microsaccade motion artifacts corrected by the registration algorithm. It was found that 100% of large movement artifacts were successfully removed in 50 y-fast scans of normal eyes and 20 y-fast scans of eyes with PDR. When microsaccade motion artifacts are overlapped between the two y-fast scans (FIGS. 16A-B), an interpolation process was applied. The motion artifact overlap was filled based on neighboring pixels. Since the number of missing lines is only 1 or 2 in all the scans processed in this study and interpolation can achieve seamless filling (FIG. 16C), the overlap of microsaccades is not problematic for the system. It should be noted that the residual variation in the vessel brightness between lines is due to the uneven number of original scans merged in the final en face OCTA. For example, the lines registered and merged from two scans show more capillary network and the lines composed of only one scan show less capillary network.

To quantitatively evaluate how fine registration improves the image contrast, the root mean square (RMS) contrast was used. RMS contrast is defined as the standard deviation of the decorrelation value as follows:

$$C_{RMS} = \sqrt{\frac{1}{A} \times \sum_{(x,y)\in A} (M(x, y) - \overline{M})^2} \qquad (11)$$

where A is the area of the merged image, M(x,y) is the decorrelation value of coordinate (x,y) and $\overline{M}$ is the mean decorrelation value of the entire merged image. Comparison of the $C_{RMS}$ before and after fine registration was performed on all 6×10 mm en face OCTA in this study. The improvement of contrast is shown in Table 1.

TABLE 1

The Comparison of the RMS Contrast

| RMS contrast (mean ± sd) | Before fine registration | After fine registration | Improvement |
|---|---|---|---|
| Normal | 0.18 ± 0.03 | 0.25 ± 0.03 | 35.5% |
| PDR | 0.19 ± 0.02 | 0.25 ± 0.04 | 31.8% |

Figure 17:
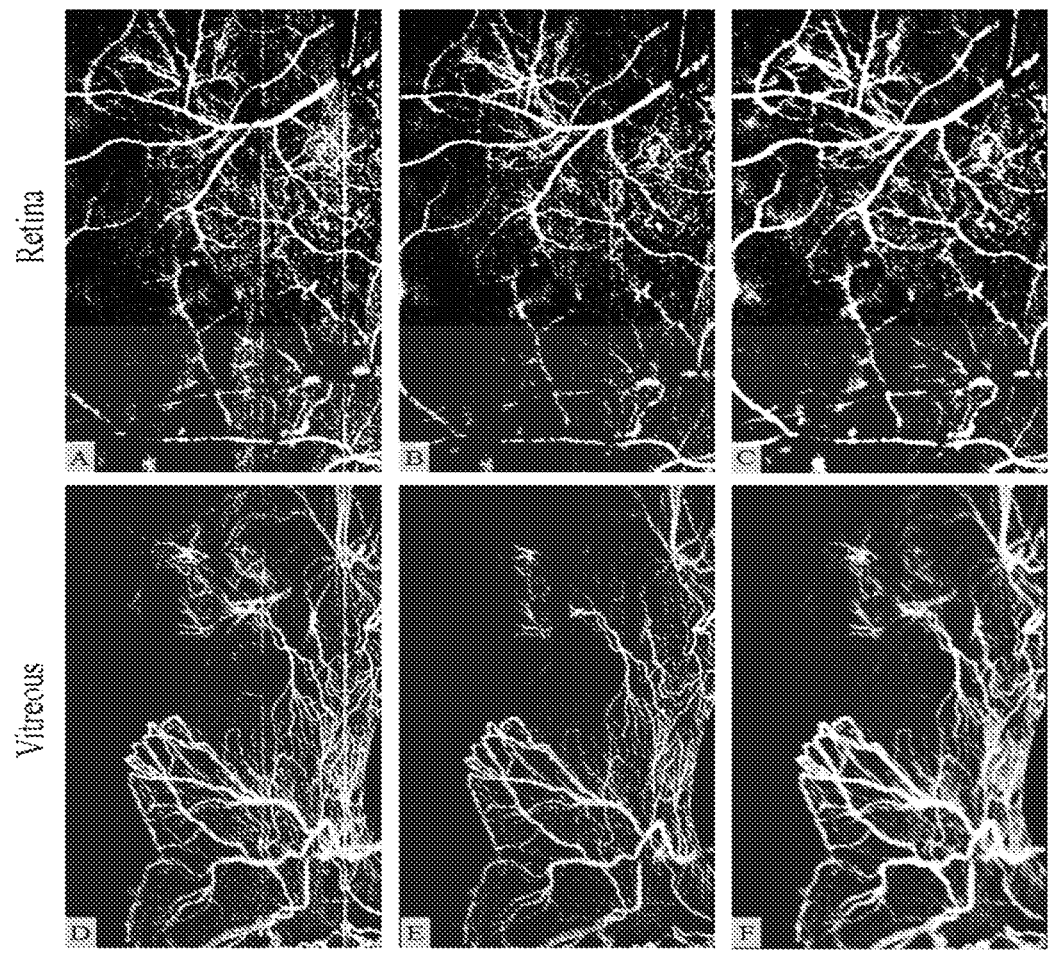
FIGS. 17A-17F are a set of images showing the registration of two y-fast en face OCTA images from an eye with proliferative diabetic retinopathy (PDR). The size of the imaged region is 6 mm×10 mm.

To test the applicability of the disclosed systems and methods in a clinical setting, datasets obtained from patients with PDR were analyzed. The eye of PDR is characterized by heterogeneous vasculature with areas of drop out as well as proliferation of new vessels that are present above the ILM (e.g., within the vitreous slab). Proliferative vasculature in the vitreous slab was registered and merged according to the deformable field obtained from the registration of the retina layer (FIG. 17). After motion removal and registration, the nonperfusion areas are more distinctive and the neovascular network is more continuous, compared to the original non-registered images.

Figure 18:
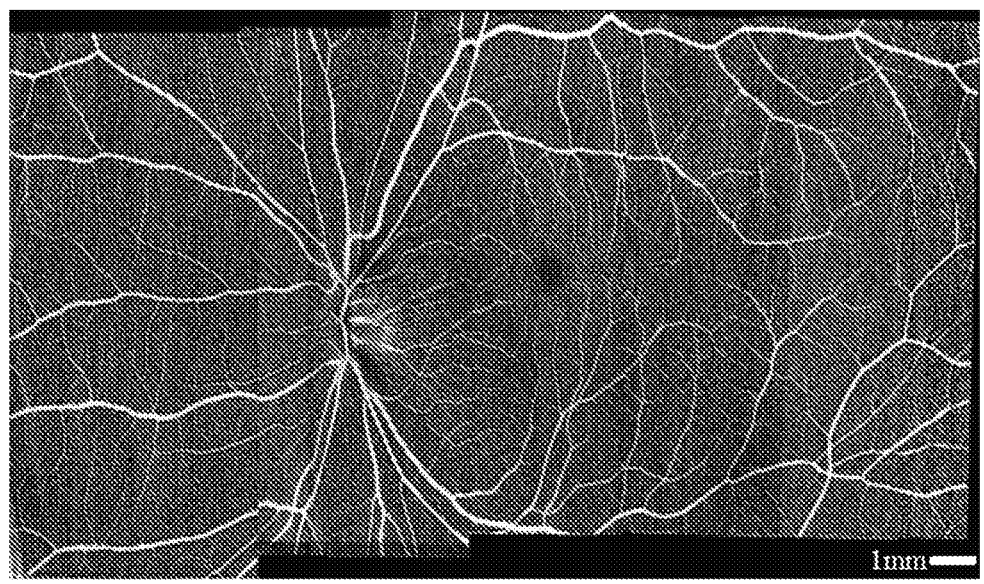
FIG. 18 is an image showing an ultrawide-field montage (23×10 mm) automatically generated by registering and merging five motion-corrected wide-field images (6×10 mm).

The ability of the disclosed methods to perform automated ultrawide-field montage using the same registration scheme was also demonstrated. FIG. 18 shows a 23×10 mm ultrawide-field OCTA of retinal vasculature in a normal subject. As shown in in the montaged image, the integrity of retinal vasculature throughout the entire posterior pole of the eye was well-recovered by registration process. Qualitatively, the montaged angiogram image is homogenous.

Example 2

Figure 19:
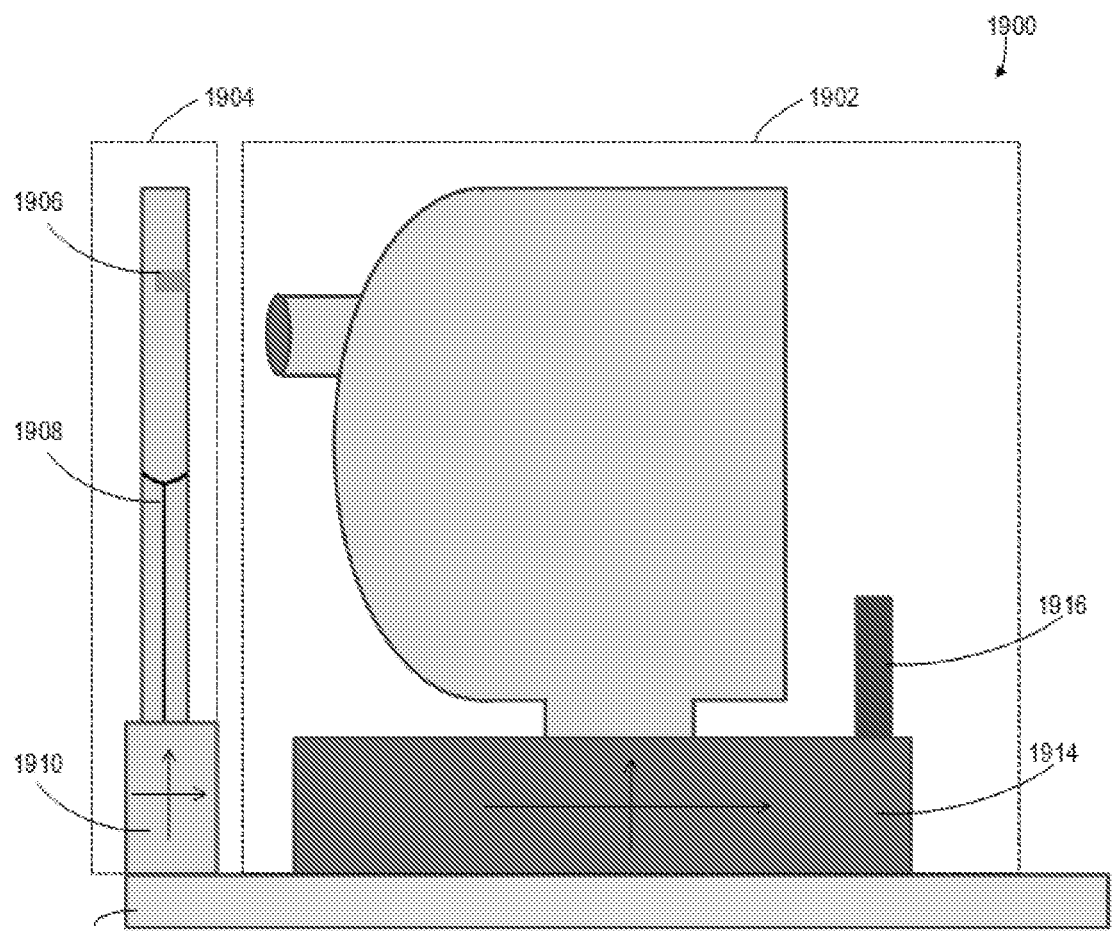
FIG. 19 is a schematic diagram of an example imaging system in accordance with the disclosure.

FIG. 19 illustrates a schematic diagram of an example imaging system 1900 in accordance with embodiments of the present disclosure. The system is comprised of a patient imaging unit 1902 and a chin/forehead rest frame 1904 configured to allow alignment and imaging of the patient eye. The patient imaging unit 1902 may contain, in a non-limiting embodiment, the components necessary to perform wide-field OCT-based imaging of the eye including imaging optics subsystem, a beam scanning subsystem, an eye fixation subsystem, an iris (pupil) camera subsystem, a line-illumination subsystem, and controlling units for the each of the subsystems. To facilitate alignment of the patient imaging unit 1902 to the eye being imaged, the patient imaging unit can incorporate a first three-axis translational stage 1914 configured to automatically adjust position based on signals received from the controlling units within the patient imaging unit 1902. The first three-axis translational stage 1914 may also be configured, in embodiments, with a manual control component 1916, for example a joystick, to allow the user to manually adjust the position of the first three-axis translational stage 1914 and thereby align the patient imaging unit 1902 to the patient eye. In embodiments, the first three-axis translational stage 1914 may be mounted to a baseplate 1912 such that the patient imaging module 1902 translates relative to the baseplate 1912. In embodiments, the chin/forehead rest frame 1904, comprising a forehead rest 1906, a chin rest 1908, and second three-axis translational stage 1910, may be mounted to baseplate 1912. In embodiments, the second three-axis translational stage may be configured to receive signals from the patient imaging module 1902 or other controller units to effect automatic position adjustment of the patient eye relative to the patient imaging module 1902. As an example, the system can be configured to automatically adjust the height and position of the chin/forehead rest 1904 through signals sent to the second three-axis translational stage 1910 in order to center the pupil of the eye 104 and adjust the distance to the iris plane 106 as described herein.

Figure 20:
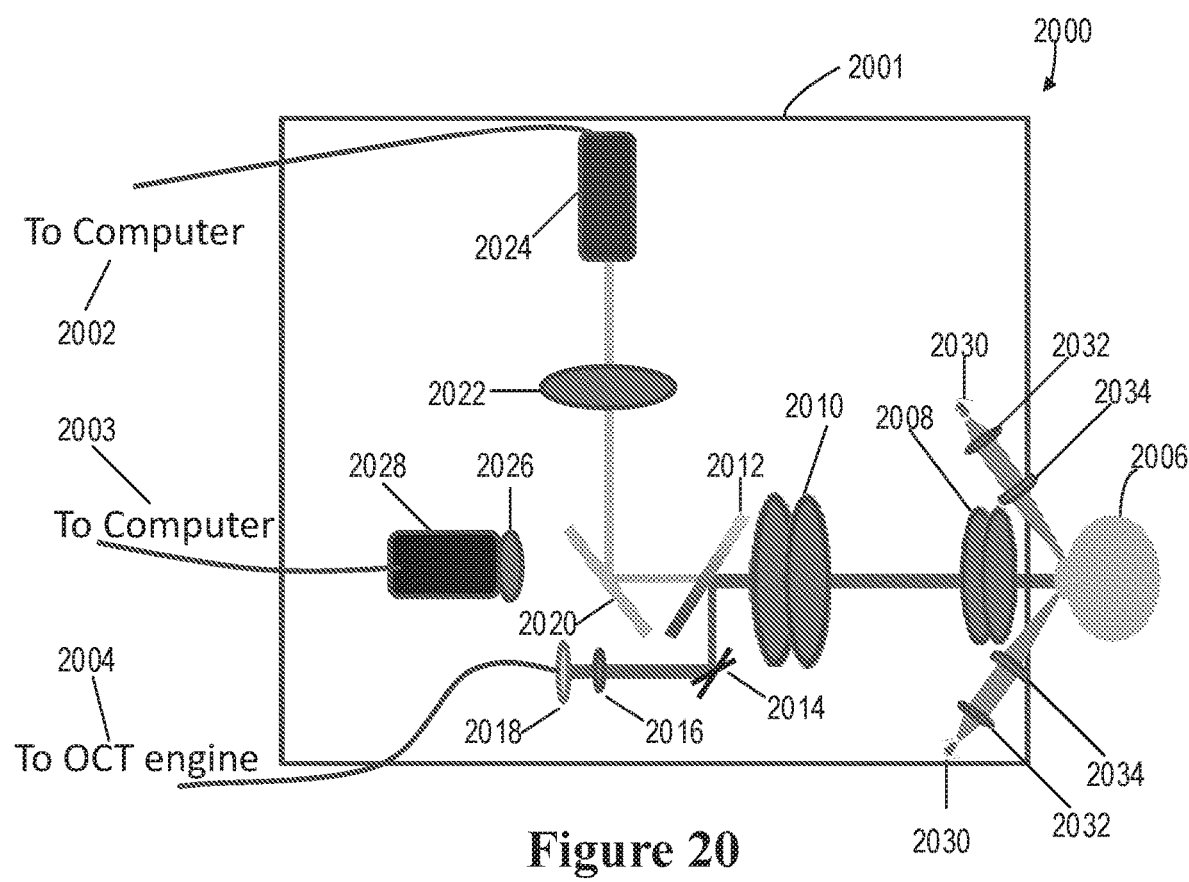
FIG. 20 is a schematic diagram of an example optics and component layout for an imaging system in accordance with the disclosure.

FIG. 20 schematically illustrates a diagram of an example imaging system components 2000 in accordance with embodiments of the imaging system of the present disclosure. At 2001 a set of components that may be included in an example, non-limiting, optics layout are specified. In embodiments, these optical components may be housed within, for example, the patient imaging unit 1902. An example optical path dedicated to OCT imaging of the eye 2006 may comprise a first achromatic doublet 2008 and a second achromatic doublet 2010 in line with a dichroic mirror 2012 that routes the OCT light signal to a two-axis scanning galvanometer mirror positioning system 2014. The OCT light signal path may further comprises an electrical tunable lens 2016 and collimator 2018. The OCT light signal path may be passed to an OCT engine 2004. Any suitable OCT engine may be utilized, including spectral domain and swept source OCT systems, as will be understood by those of skill in the art.

The example imaging system 2000 may also include components dedicated to fixation target presentation, pupil alignment and centering, and iris-plane positioning of the scanning beam pivot point. For example, components of an eye fixation subsystem may include a beam splitter 2020, lens 2022, and a projector 2024 for presentation of a fixation target. The fixation system may include connection to a controller such as a computer 2002 to present different fixation targets during data acquisition. Components of an example pupil alignment and centering system may include a lens 2026, a camera 2028, and connection to a controller such as a computer 2003. The camera may be positioned and configured to capture a sequence of images of the iris and pupil of the eye, which may be further processed by the controller computer 2003 and used to effect centering of the pupil. For example, based on analysis of the captured image sequence from camera 2028 by the controller computer 2003, the system may be configured to adjust the position of the chin/forehead rest frame 1904 by actuation of translational stage 1910 or the position of the patient imaging unit by actuation of translational stage 1914. Components of an example an iris-plane positioning system to optimize location of the scanning beam pivot point may include a light source (for, example an LED) 2030, a collimator 2034, a cylindrical lens 2036, a camera 2028, and connection to a controller such as a computer 2003. The camera 2028 may be positioned and configured to capture a sequence of images of an illumination line cast on the iris of the eye 2006 by the cylindrical lens 2036. Based on analysis of the captured illumination line image sequence by the controller computer 2003, the system may be configured to adjust the distance between the iris plane and lens 2008 via movement of translational stages 1910 and/or 1914. In embodiments, the controller computers 2002 and 2003 may be the same units or may be separate units. In embodiments, the controller computers 2002 and 2003 and the OCT engine 2004 may be located either within or external to the patient imaging unit 1902.

Example 3

Optical Coherence Tomography Angiography Image Processing System

Figure 21:
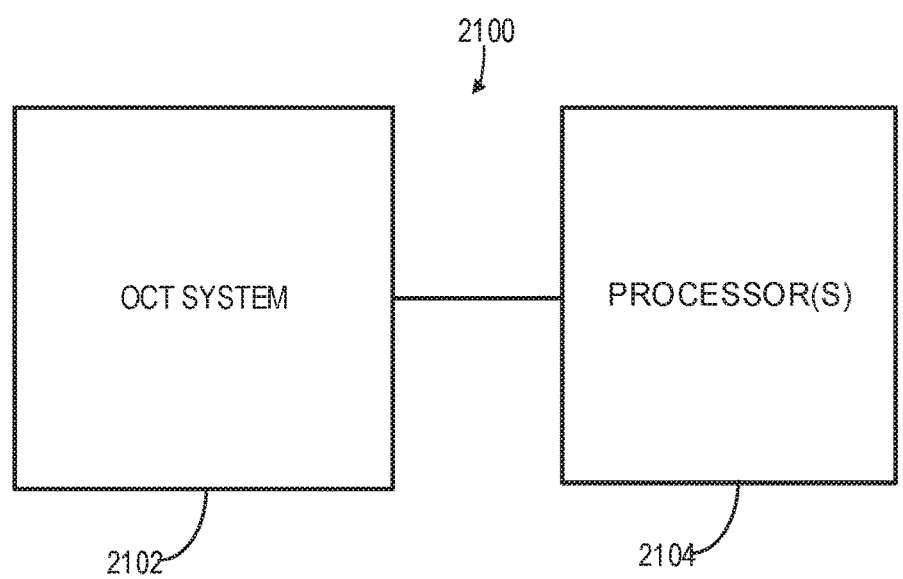
FIG. 21 is a schematic of an example system for processing widefield OCT datasets in accordance with the disclosure.

FIG. 21 schematically shows an example system 2100 for OCT image processing in accordance with various embodiments. System 2100 comprises an OCT system 2102 configured to acquire an OCT image comprising OCT interferograms and one or more processors or computing systems 2104 that are configured to implement the various processing routines described herein. OCT system 2100 can comprise an OCT system suitable for OCT angiography applications, e.g., a swept source OCT system or spectral domain OCT system.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., the methods depicted in FIG. 1, FIG. 5 and FIG. 7 described above, can be implemented as a computer application, computer service, computer API, computer library, and/or other computer program product.

Figure 22:
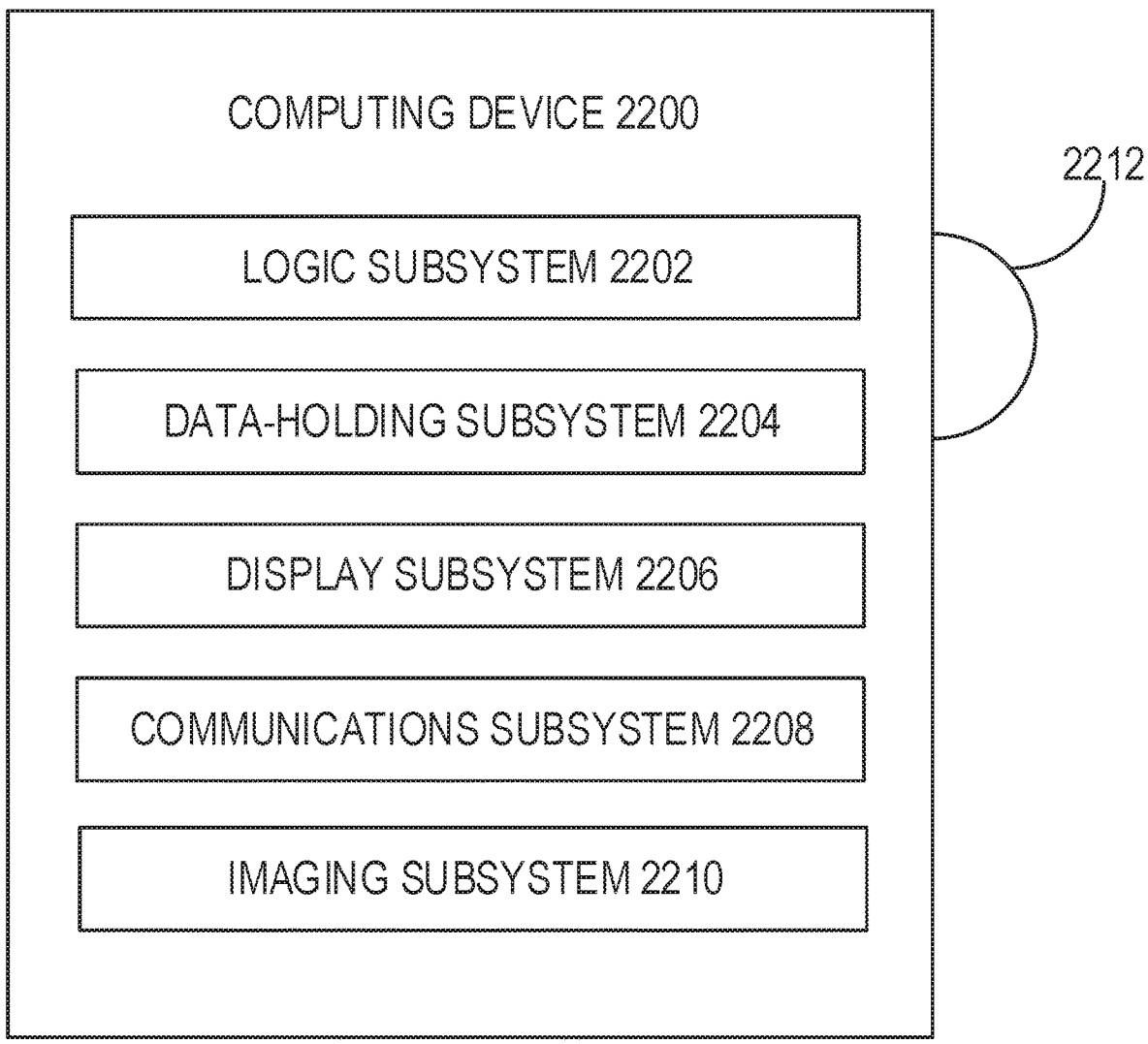
FIG. 22 is a schematic of an example computing system in accordance with the disclosure.

FIG. 22 schematically shows a non-limiting computing device 2200 that can perform one or more of the methods and processes described herein. For example, computing device 2200 can represent a processor included in system 2000 or system 2100 described above, and can be operatively coupled to, in communication with, or included in an OCT system or OCT image acquisition apparatus. Computing device 2200 is shown in simplified form. It is to be understood that virtually any computer architecture can be used without departing from the scope of this disclosure. In different embodiments, computing device 2200 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 2200 includes a logic subsystem 2202 and a data-holding subsystem 2204. Computing device 2200 can optionally include a display subsystem 2206, a communication subsystem 2208, an imaging subsystem 2210, and/or other components not shown in FIG. 22. Computing device 2200 can also optionally include user input devices such as manually actuated buttons, switches, keyboards, mice, game controllers, cameras, microphones, and/or touch screens, for example.

Logic subsystem 2202 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 2204 can include one or more physical, non-transitory, devices configured to hold data and/or instructions executable by the logic subsystem to implement the herein described methods and processes. When such methods and processes are implemented, the state of data-holding subsystem 2204 can be transformed (e.g., to hold different data).

Data-holding subsystem 2204 can include removable media and/or built-in devices. Data-holding subsystem 2204 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 2204 can include devices with one or more of the following characteristics: volatile, nonvolatile, dynamic, static, read/write, read-only, random access, sequential access, location addressable, file addressable, and content addressable. In some embodiments, logic subsystem 2202 and data-holding subsystem 2204 can be integrated into one or more common devices, such as an application specific integrated circuit or a system on a chip.

FIG. 22 also shows an aspect of the data-holding subsystem in the form of removable computer-readable storage media 2212, which can be used to store and/or transfer data and/or instructions executable to implement the herein described methods and processes. Removable computer-readable storage media 2212 can take the form of CDs, DVDs, HD-DVDs, Blu-Ray Discs, EEPROMs, flash memory cards, USB storage devices, and/or floppy disks, among others.

When included, display subsystem 2206 can be used to present a visual representation of data held by data-holding subsystem 2204. As the herein described methods and processes change the data held by the data-holding subsystem, and thus transform the state of the data-holding subsystem, the state of display subsystem 2206 can likewise be transformed to visually represent changes in the underlying data. Display subsystem 2206 can include one or more display devices utilizing virtually any type of technology. Such display devices can be combined with logic subsystem 2202 and/or data-holding subsystem 2204 in a shared enclosure, or such display devices can be peripheral display devices.

When included, communication subsystem 2208 can be configured to communicatively couple computing device 2200 with one or more other computing devices. Communication subsystem 2208 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 2200 to send and/or receive messages to and/or from other devices via a network such as the Internet.

When included, imaging subsystem 2210 can be used acquire and/or process any suitable image data from various sensors or imaging devices in communication with computing device 2200. For example, imaging subsystem 2210 can be configured to acquire OCT image data, e.g., interferograms, as part of an OCT system, e.g., OCT system 2102 described above. Imaging subsystem 2210 can be combined with logic subsystem 2202 and/or data-holding subsystem 2204 in a shared enclosure, or such imaging subsystems can comprise periphery imaging devices. Data received from the imaging subsystem can be held by data-holding subsystem 2204 and/or removable computer-readable storage media 2212, for example.

Example 4

3D Registration Algorithm

Study Population

This study was conducted at the Casey Eye Institute at the Oregon Health & Science University. The study adhered to the tenets of the Declaration of Helsinki and was approved by the Institutional Review Board. Six healthy participants (age, 35±4 years) were recruited to the study.

Image Acquisition

A 200-kHz prototype swept-source OCT system was used in this study. The source laser had a center wavelength of 1045 nm and a tuning range of ~100 nm (Axsun Technologies Inc., Billerica, Mass.). A dual-balanced detector (PDB471C, Thorlabs Inc) converted the optical signal to electrical signal, and a high speed digitizer (ATS 9360, Alazar Technologies Inc., Pointe-Claire, QC) acquired the electrical signal. The resulting system had an axial resolution of 7.5 µm in air, a lateral resolution of 12 µm, and an extended axial imaging range of 7 mm. The light exposure at the cornea was 1.4 mW, within the American National Standards Institute safety limit.

Two 6×10×7 (x×y×z) mm volumetric y-fast scans were captured at the same region of posterior pole including the macula and the disc in each eye. Each volume consisted of 800 B-frames, composed of a set of 850 A-lines acquired twice at each of the 400 raster positions. This yielded a lateral sampling density of 11.8 µm along the fast transverse scan axis and 15.0 µm along the slow axis. One volumetric scan was acquired in approximately 4 seconds.

Structural OCT data was obtained by averaging the two B-frames acquired at the same raster position. The split-spectrum amplitude-decorrelation angiography (SSADA) algorithm (e.g., as described in Y. Jia, O. Tan, J. Tokayer, B. Potsaid, Y. Wang, J. J. Liu, M. F. Kraus, H. Subhash, J. G. Fujimoto, J. Hornegger, and D. Huang, "Split-spectrum amplitude-decorrelation angiography with optical coherence tomography," Opt. Express 20(4), 4710-4725 (2012), incorporated by reference herein) calculated OCTA data. The boundaries of ILM and outer plexiform layer (OPL) were detected on each B-frame by directional graph search method (e.g., as described in M. Zhang, J. Wang, A. D. Pechauer, T. S. Hwang, S. S. Gao, L. Liu, L. Liu, S. T. Bailey, D. J. Wilson, D. Huang, and Y. Jia, "Advanced image processing for optical coherence tomographic angiography of macular diseases," Biomed. Opt. Express 6(12), 4661-4675 (2015), incorporated by reference herein). The en face retinal angiogram was generated by using the maximum decorrelation value along the axial direction within a slab between ILM and OPL.

Volumetric Registration Algorithm

Figure 23:
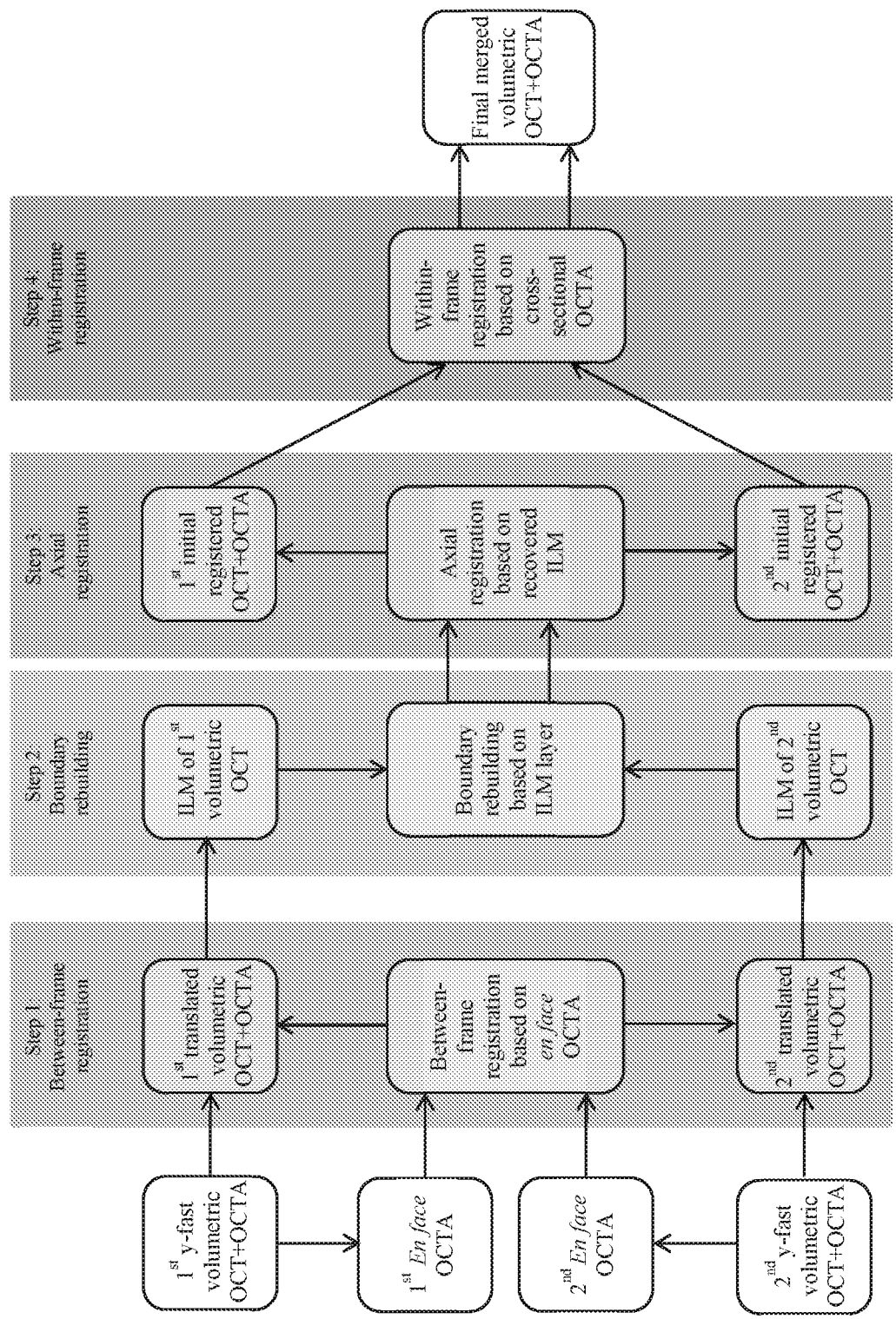
FIG. 23 is a flow chart of a 3D registration and volume rebuilding algorithm in accordance with various embodiments.
Figure 24:
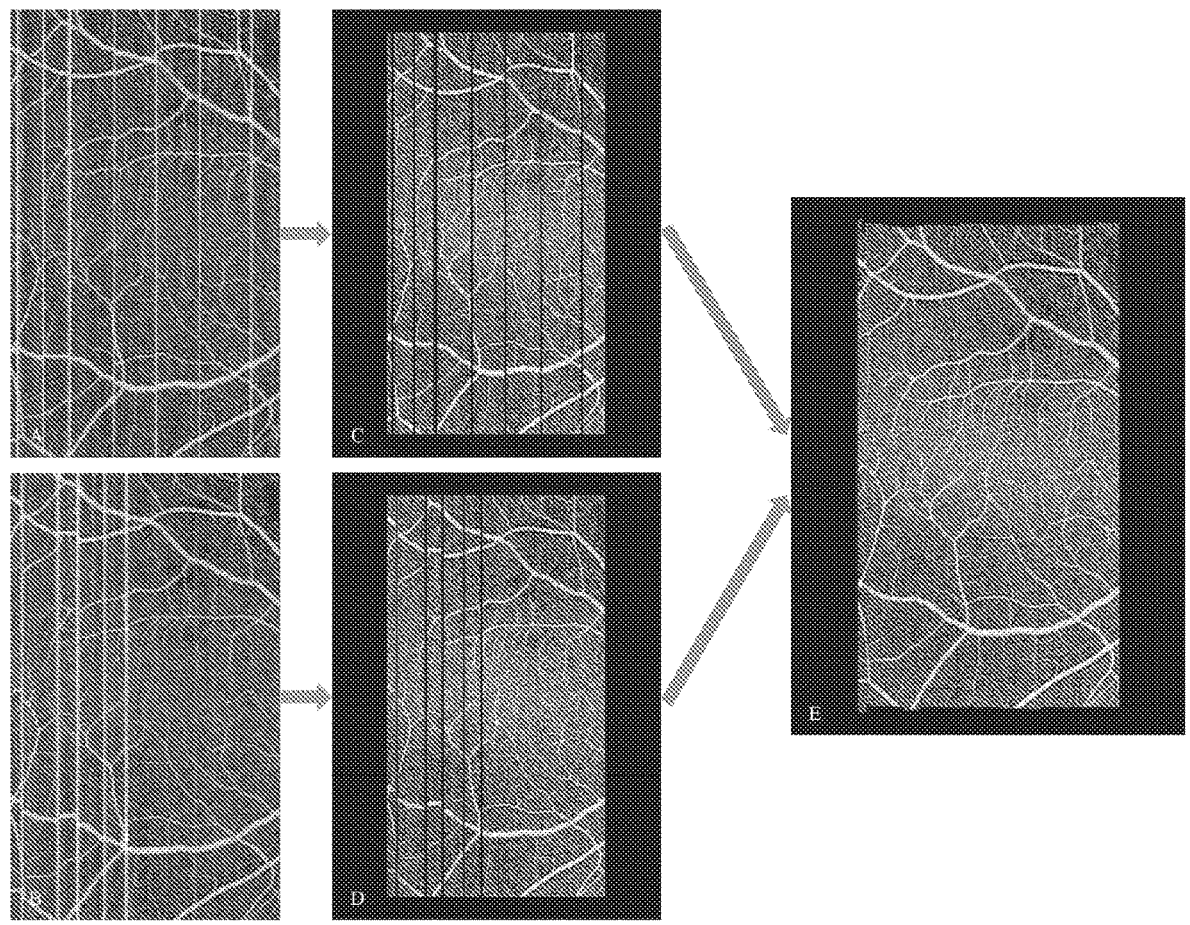
FIGS. 24A-E depict a schematic diagram of the between-frame registration process between 2 y-fast volumetric scans.

A flowchart of the 3D volumetric registration method used in this example is shown in FIG. 23. First, the transverse motion artifacts on en face retinal OCTA is corrected by affine registration algorithm on the parallel microsaccade-free strips. This operation corrects the motion artifacts between B-frames caused by translational, rotational and focusing differences (see FIG. 24). Each A-line of reflectance and decorrelation signal in the volumetric OCT is translated based on the transformation matrix of the corresponding strip. Then, the ILM boundaries on the new transformed slow-axis B-frames at the same position in each volume are averaged and smoothed to recover a motion-free ILM boundary. Based on this new boundary, each pair of A-lines was initially registered along axial direction at each B-frame. The final axial position of each A-line was fine-tuned by correlation of reflectance of each pair of A-lines. Next, a registration based on cross-sectional OCTA was applied between each pair of fast-axis B-frame to refine the final transverse position of each A-line. Then, two volumes of structural OCT and OCTA are averaged and merged respectively to produce the final motion-corrected volumes.

Between Frame Registration

In various embodiments, the large motion artifacts shown as bright lines on en face OCTA were detected and removed. The algorithm detected these bright line artifacts as projected B-frames with summed flow signal above the threshold (e.g., set as 2.3 standard deviations above the mean). Then en face angiogram was divided into microsaccade-free strips at the detected motion lines (FIGS. 24C and 24D). The registration process was initiated on two strips, one from each scan, that contain the largest overlap. Using the larger of the two strips as the reference strip and the other the moving strip, the affine registration algorithm was applied. The affine registration algorithm may utilize a gradient descent to search for a similarity transformation which allows translation, scaling, rotation, and skewing within the transverse (x-y) plane. The goal is to find a transformation of the moving strip that minimizes the squared difference of the reference vasculature and transformed moving vasculature $$C_{between}(t) = \sum_{x,y} [V_r(x,y) - V_m(T(x,y;t))]^2 \qquad (12)$$

where (x, y) is the pixel coordinate; t is a vector of transformation parameters; $V_r$ (x, y) is reference vasculature; $V_m$ (x, y) is moving vasculature; T is the transformation matrix. This minimization can be solved iteratively. The new registered and merged strip was then defined as the new reference strip and the strip with the largest overlap with the new reference strip as the new moving strip. The process was repeated until all strips are registered and merged into one comprehensive en face OCTA image (FIG. 24E).

This operation provides the transverse transform matrix. Each A-line of the $1^{st}$ and $2^{nd}$ volumetric structural OCT and OCTA was translated and the between-frame transformation was completed.

Rebuilding of the Internal Limiting Membrane Boundary

Figure 3B:
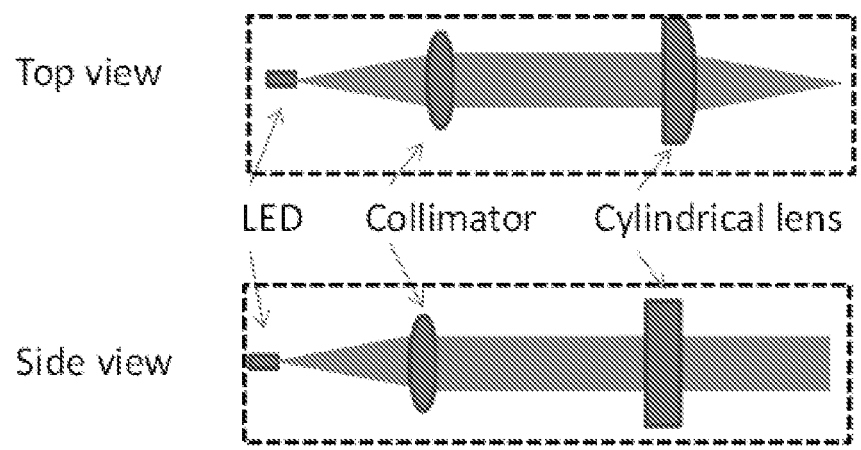
FIG. 3B is a schematic of an example optics layout for a line illumination system configured to produce a vertical line on the iris of the eye.
Figure 25:
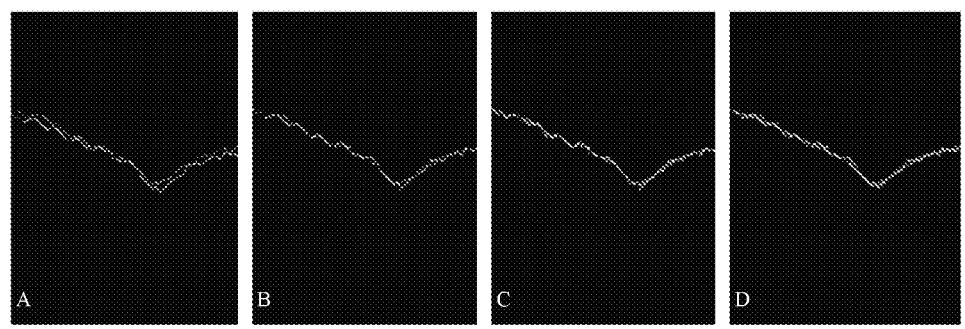
FIGS. 25A-25D illustrate the rebuilding process of the ILM boundary height profile along the x (slow) axis.

Next, the ILM boundary was rebuilt by merging and smoothing ILM boundaries on two transformed volumetric structural OCT. This rebuilding process was performed in the slow-axis. A pair of slow-axis ILM boundaries from each volume was adjusted to the closest position (FIGS. 3A and 3B). In this operation, the ILM boundary from the reference volume is the reference boundary $B_r$, the ILM boundary from moving volume is the moving boundary $B_{m_0}$. The newly moved boundary $B_m$ was obtained when the moving boundary adjusted to the closest position to the reference boundary based on Eq. 13:

$$B_m(x) = B_{m_0}(x) + t \quad x = 1, 2, \ldots, L \qquad (13)$$

$$E = \sum_{i=1}^{L} |B_r(i) - B_m(i)| \quad B_r(i) > 0, B_m(i) > 0$$

$$t^* = \operatorname{argmin}(E \mid t) \quad t \in [-100, 100]$$

where t is the displacement of the $B_{m_0}(x)$, E is the cost function, L is the number of the A-line in corresponding slow-axis B-frame and the optimized displacement t is selected when the cost function E achieves the smallest value. The height profiles of reference boundary and the moved boundary were averaged to generate the initial merged ILM boundary $B_{ave}$ (FIG. 25C)

$$B_{ave} = (B_r + B_m)/2 \qquad (14)$$

Then, the final rebuilt ILM boundary of this B-frame was obtained after a smoothing process on $B_{ave}$ according to Eq. 15:

$$B_{rebuilt} = \qquad (15)$$

$$\begin{cases} B_{rebuilt}(n) = B_{ave}(1) + \ldots + & n \in [1, sp] \\ B_{ave}(n) + \ldots + B_{ave}(n+n-1) & \\ B_{rebuilt}(n) = B_{ave}(n-sp) + \ldots + & n \in [sp+1, L-sp] \\ B_{ave}(n) + \ldots + B_{ave}(n+sp) & \\ B_{rebuilt}(n) = B_{ave}(n-(L-n)) + \ldots + & n \in [L-sp+1, L] \\ B_{ave}(n) + \ldots + B_{ave}(L) & \end{cases}$$

$$sp = \lfloor L/20 \rfloor$$

where sp is the smooth parameter and $\lfloor \ \rfloor$ means round down (FIG. 25D).

Axial Registration

Figure 26:
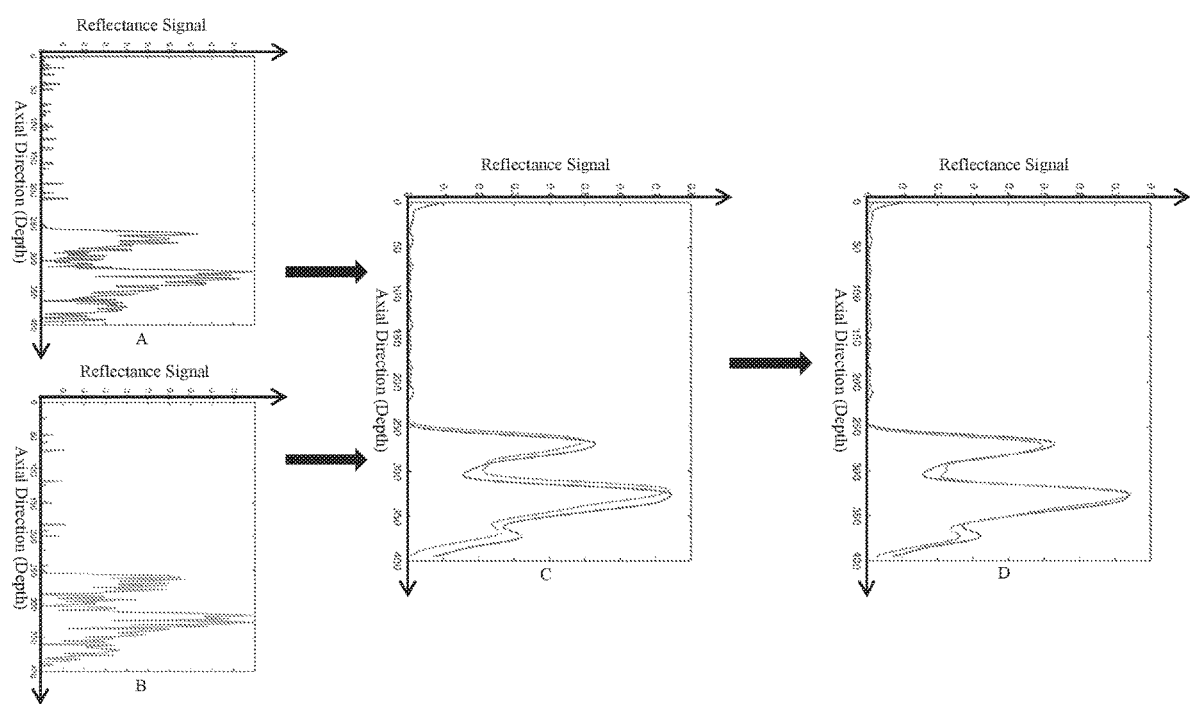
FIGS. 26A-26D illustrate an axial registration process in accordance with various embodiments.

After the rebuilt ILM boundary was obtained, each A-line of two OCT & OCTA volumes was translated based on the displacement between $B_{rebuilt}$ and corresponding ILM boundary according to Eq. 16:

$$D_r(x,y)=B_{rebuilt}(x,y)-B_r(x,y)$$

$$D_m(x,y)=B_{rebuilt}(x,y)-B_m(x,y) \quad (16)$$

where $D_r(x, y)$ and $D_m(x, y)$ are the displacement of each A-line respectively in reference and moving volumes, (x,y) is the coordinate of each A-line. Each A-line was then translated based on the corresponding displacements. To reduce the registration error caused by ILM segmentation, another registration between these two A-lines was applied to fine-tune the axial final positions. Before the registration, the reflectance of two A-lines (FIGS. 26A and 26B) were first normalized to [0,1] and filtered by a $1 \times N_z$ pixel Gaussian filter with 5 pixel standard deviation (FIG. 26C). The registration was optimized by a cost function C(p) according to Eq. 17:

$$C(p) = \frac{1}{N_z} \sum_{z=1,2,\ldots,N_z} [A_r(z) - A_m(z+p)]^2 \quad p = [-10, 10] \quad (17)$$

where C(p) is the cost function of the registration, $A_r(z)$ is the normalized reflectance of the reference A-line, $A_m(z+p)$ is the normalized reflectance of the moving A-line after a displacement p and $N_z$ is the number of pixel in each A-line. The optimized displacement P was selected when the cost function C(p) achieves the smallest value. In the final axial registration step, $A_r(z)$ and $A_m(z)$ was translated to $A_r(z-(p^*-\lfloor p^*/2 \rfloor))$ and $A_m(z+\lfloor p^*/2 \rfloor)$, respectively (FIG. 26D).

Within-Frame Registration

To further improve the transverse registration accuracy, a within-frame registration based on the cross-sectional decorrelation signal profile was performed.

Figure 27:
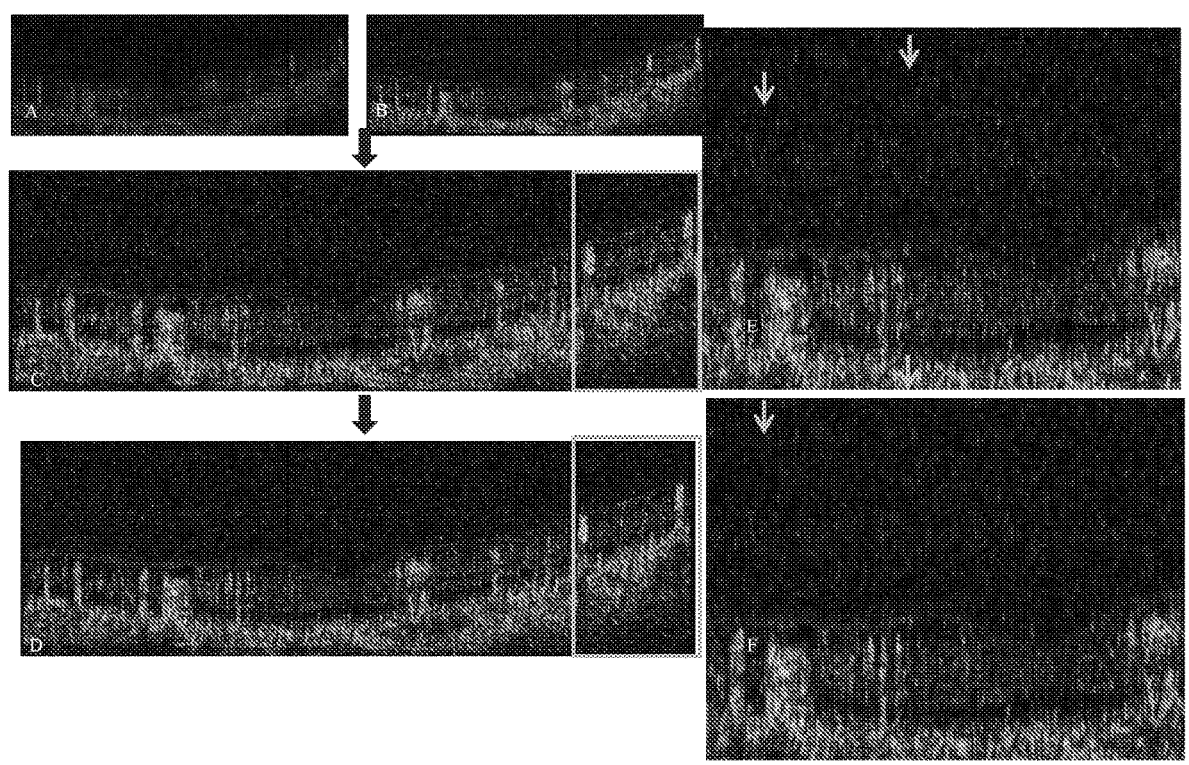
FIGS. 27A-27D. illustrate an example of the within-frame registration between a pair of OCTA B-frames.
FIG. 27E illustrates an enlargement of FIG. 27C showing mismatch in the position of two large vessels (indicated by arrows).
FIG. 27F illustrates an enlargement of FIG. 27D showing registration of the two mismatched vessels.

The decorrelation signal on each pair of B-frame along y (fast) axis was registered by an affine registration (FIG. 27). Since there were just some small distortions between two initially registered volumes, the ranges of translation, scale, rotation and skew were limited to |translation|<5, |scale−100%|<5%, |rotation|<2° and |skew−90°|<3°.

After the within-frame registration, the final merged volumetric scans were obtained by averaging two registered OCT & OCTA volumes together. And a post-processing including Gabor filter and multiscale vessel enhancement filter was performed to improve the image quality of the en face OCTA.

Evaluations

The automated volumetric registration of two scans took average 7 minutes. The test was performed on a workstation with Inter(R) Xeon(R) CPU E3-1226 v3 @ 3.30 GHz and 16.0 GB RAM using MATLAB 2014b (Mathworks, Natick, Mass.).

Figure 28:
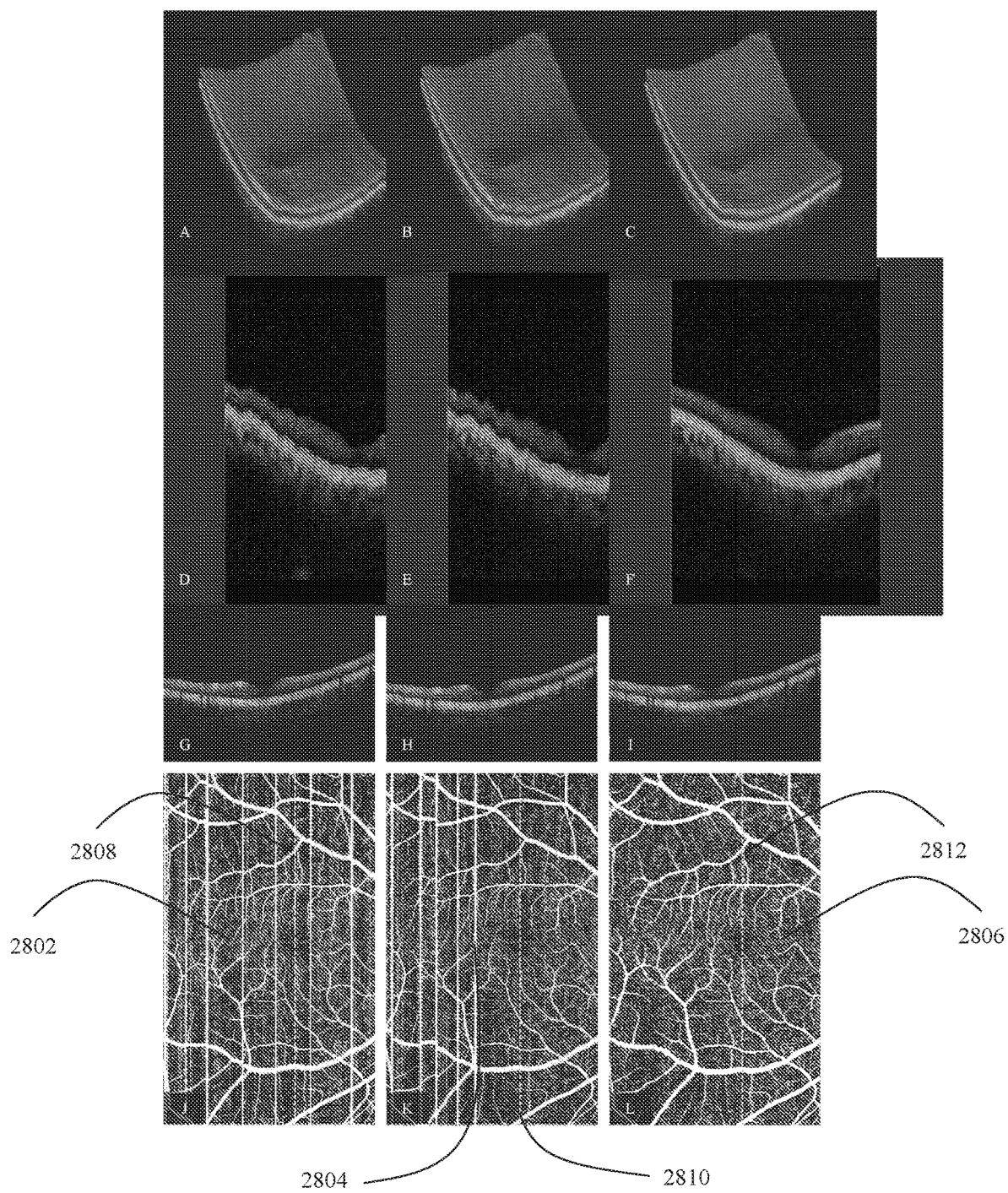
FIGS. 28A-28L depict 3D registration of two y-fast volumetric OCT & OCTA (6×10×7 mm) of macular region on a normal eye.

FIGS. 28A-28L show the registration results of two y-fast scans on central macula. The volumetric rendering of the scan volumes (first row) before and after motion correction shows the surface ripples due to axial motion on the original y-fast volume (FIGS. 28A and 28B). The correction recovers the smoothness of volume surface (FIG. 28C). B-frames on slow-axis, seen on the second row, also show the performance of axial registration. The microsaccades along axial direction distort the retinal and choroidal layers in the original B-frames (FIGS. 28D and 28E). Axial registration recovers the smooth boundaries of retina and choroid, including the outer boundary of the choroid (FIG. 28F). No motion artifact is shown on B-frames along y (fast) axis (FIGS. 28G and 28H) due to the high A-line rate on the vertical priority. Our results show no registration error is introduced on fast-axis in the merged B-frame (FIG. 28I), although the axial registration is performed on slow-axis. In addition, the transverse motion artifacts and the vasculature incoherence are all corrected on OCTA (FIG. 28J-28L).

Figure 29:
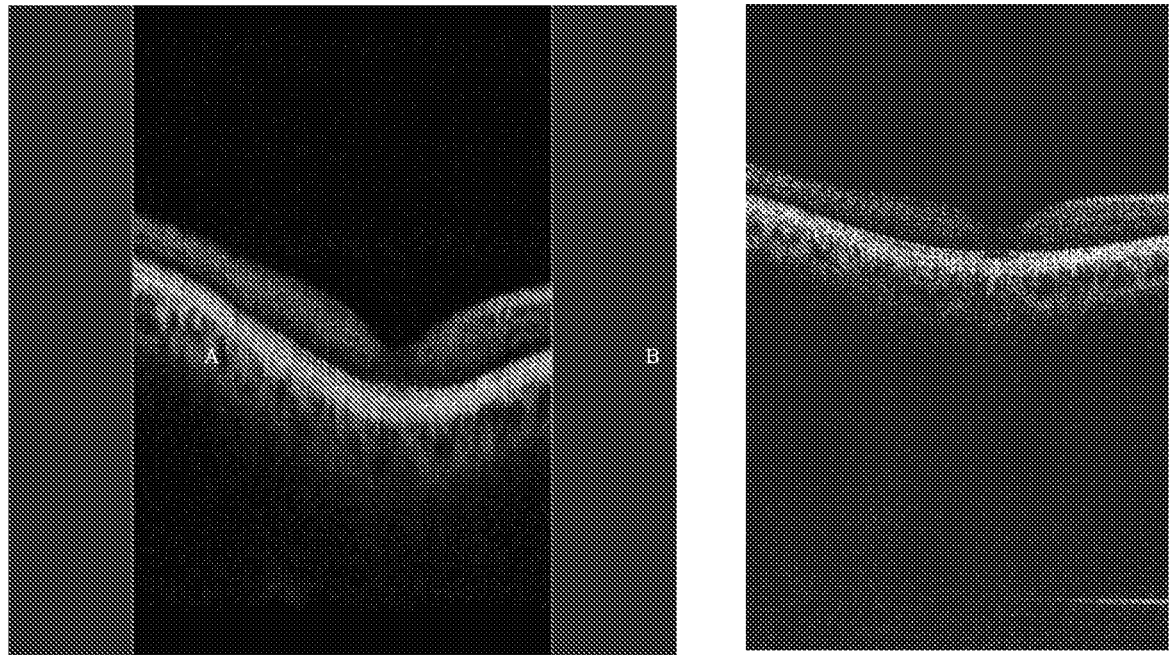
FIGS. 29A-29B illustrate a comparison of the slow-axis B-frame of the merged OCT in FIG. 29A and the x-fast B-frame crossing the fovea in FIG. 29B, which represents the true contour of the retina.

FIG. 29 shows that the registered and merged structural B-frame on slow axis crossing fovea mimics the B-frame acquired by x-fast scan on the same position of the same eye, indicating that the axial registration based on ILM boundary rebuilding on slow axis resembles the anatomic retinal contour.

Figure 30:
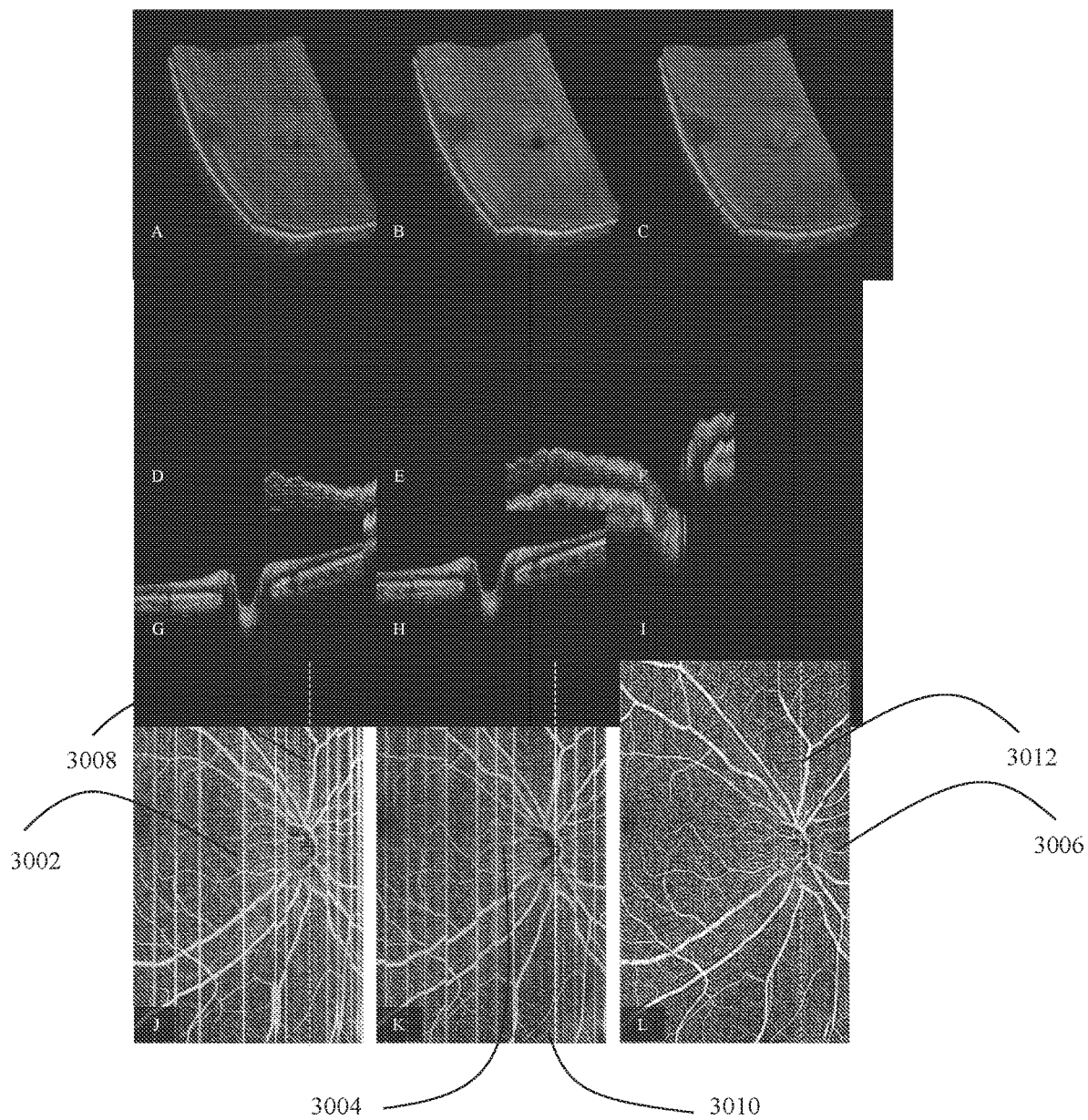
FIGS. 30A-30L illustrate 3D registration of two y-fast volumetric OCT & OCTA (6×10×7 mm) of disc region on a normal eye.
Figure 31:
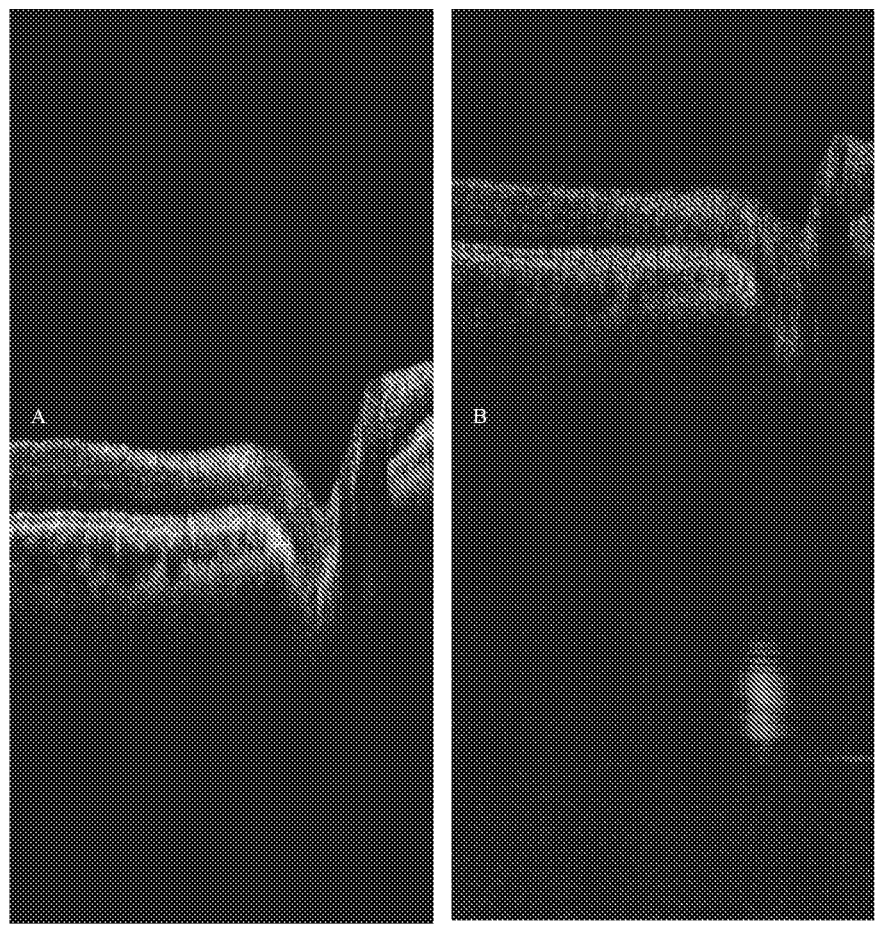
FIG. 31 illustrates a comparison of the slow-axis of the merged OCT in FIG. 31A and the x-fast B-frame across the optic nerve head in FIG. 31B, which represents the true contour of the retina.

The registration results on a scan that includes the optic nerve head, which is more complex than the fovea, further demonstrate the stability and adaptability of this method. The registration performance can be globally reviewed by volumetric rendering of the scan volumes before and after registration (FIGS. 30A-30C). The registered volume shows the even and regular appearance of the optic nerve head and surrounding retina structures. The distorted cross-sectional B-frames on slow-axis in the original volumes were corrected in the registered volume (FIGS. 30D-30F). The image contrast of retinal layers and its microstructures are enhanced. Similar to the original fast-axis B-frames, the registered and merged B-frame shows no translation artifacts (FIGS. 30G-30I). En face OCTA after registration shows more continuous and distinctive vasculature than that in the non-registered volume. Again, the retinal layer profiles and the regular anatomic microstructures of disc shown in the merged B-frame are highly correlated to the corresponding x-fast B-frame on the same position (FIG. 31).

To quantitatively evaluate the registration accuracy, the average pixel distance (APD) between the ILM boundary of fast-axis and the slow-axis was calculated using Eq. 18:

$$C_{APD} = \frac{1}{L}\sum_{x=1}^{L} |B_{fast-axis}(x) - B_{slow-axis}(x)| \quad (18)$$

where L is the number of the A-line in the overlap region between the fast-axis and slow-axis B-frames across foveal and disc regions, respectively. This overlap region was obtained after a rigid registration that includes translation and rotation only between a pair of fast-axis and slow-axis B-frames. This registration is also based on the affine registration using en face OCTA vascular information. To ensure the accuracy of this evaluation, only the B-frames across fovea and disc that have distinctive structure feature were chosen in this assessment. The comparison to original retinal contours (ILM along fast-axis) between registered and original slow-axis B-frames is shown in Table 2.

TABLE 2

The Comparison of average pixel distance (APD) to fast-axis B-frames on slow-axis B-frames before and after registration

| APD (mean ± sd, n = 6) | Before registration | After registration | Decrease |
|---|---|---|---|
| Macula | 6.08 ± 0.23 | 4.80 ± 0.19 | 21.1% |
| Disc | 10.43 ± 1.68 | 7.03 ± 1.13 | 32.6% |

To quantitatively measure the improvement of contrast on en face OCTA, the root mean square (RMS) contrast [31] was used and calculated using Eq. 19:

$$C_{RMS} = \sqrt{\frac{1}{S} \times \sum_{(x,y)\in S} (V(x,y) - \overline{V})^2} \quad (19)$$

where S is the area of the merged image, V(x,y) is the en face OCTA of the inner retinal slab and $\overline{V}$ is its mean decorrelation value.

TABLE 3

The Comparison of root mean square contrast on en face OCTA before and after registration

| RMS contrast (mean ± sd, n = 6) | Before registration | After registration | Improvement |
|---|---|---|---|
| Macula | 0.214 ± 0.01 | 0.236 ± 0.01 | 10.3% |
| Disc | 0.219 ± 0.02 | 0.292 ± 0.01 | 33.1% |

These quantitative analyses demonstrate significant improvement of the retinal structural contour (Table 2) on the structural OCT and the RMS contrast (Table 3) on the en face OCTA.

Discussion

Embodiments provide a 3D registration method that removes motion artifacts and merges a volumetric angiographic and a structural OCT volume in the same transverse priority. This method is well suited for OCTA using ultrahigh-speed OCT. The algorithm effectively eliminates axial and transverse motion artifacts, resulting in smooth volume rendering and high-contrast angiography with excellent vessel continuity.

One unique attribute of this method is the use of OCTA and structural OCT information separately for transverse and axial registration. No prior techniques have used motion indicator on OCTA to guide volumetric registration. Compared to shadow-graphic pattern of large vessels on en face structural OCT, the detailed vasculature on OCT angiograms provides a better reference for transverse registration. Another advantage of using en face OCTA is that the microsaccade motions have been naturally shown as the bright motion artifact, eliminating the need to compute the cross-correlation between contiguous lines (projected B-frames) to detect this type of motion on en face structural OCT.

Unlike the previously discussed orthogonal 3D registration methods using full A-scan profiles, the 3D registration method performs transverse and axial registration separately to achieve 3D registration. This strategy allows a more efficient processing, especially on the large scan volume with large number of A-lines.

The transverse registration method in this Example differs from the previously discussed strip-based en face registration process, in that we did not apply free-form deformation which is a type of local non-rigid registration, because the translation of A-lines based on this deformation requires much computation time and memory space. Although the registration on the en face direction may not be as accurate as the work reported on 2D OCTA, by adding the within-frame affine registration based on cross-sectional flow profile between each pair of y-fast B-frames, the registration accuracy in 3D may be further improved.

In order to correct the motion in axial direction, the anatomic structure may be rebuilt on slow-axis. Even without a reference scan with different scan priority, the convergence of two B-frames on the slow axis from different OCT volume can effectively recover a smooth retinal surface. However, the notable limitation of this method is that the registered retinal surface is still a few pixels different from the true retinal contour. This deficit may not be clinically significant because the recovered contour allows for accurate segmentation of retinal sublayers and generation of high quality en face structural and angiographic images. Moreover, in this operation, it is critical to accurately trace ILM boundaries. The large gradient of reflectance between the vitreous and the ILM usually allows accurate segmentation of this boundary. In the study described in Example 4, the directional graph search method was applied to further improve the segmentation efficacy.

Furthermore, this 3D registration method is complementary to the real-time eye tracking function. Even with the acquisition of 2 volumetric scans, there is still a small probability of gaps occurring in the same place at both volumes, causing registration error and stripe defect in the merged volume. This failure probability can be reduced to near zero by combining tracking assisted scanning with registration. Therefore, the registration algorithms described herein would be useful in the correction of residual tracking error.

Accordingly, provided herein is an automated 3D registration algorithm to remove motion artifacts and merging volumetric OCT & OCTA scanned by an ultrahigh-speed swept source OCT. The motion artifacts in transverse direction may be removed using the between-frame registration and the axial location may be corrected based on the ILM boundary of the retina. Two volumetric scans may be merged after the axial registration and within-frame registration. The algorithm has been demonstrated on OCT & OCTA volume including the macula and the disc in healthy volunteers. By improving the volume rendering of the retina and the quality of OCTA, this method may improve the utility of OCT-based ocular imaging.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A system for wide-field optical coherence tomography angiography (OCTA) imaging of the retina comprising:
   an optical coherence tomography (OCT) apparatus to acquire a plurality of OCT interferograms of a retina of an eye;
   a fixation target module to set fixation targets for respective OCT interferograms of the plurality of OCT interferograms at a respective locations in a field of view;
   an eye centering module to align a center of a pupil of the eye with respect, to a scanning beam of the OCT apparatus; and an iris plane module to position the pivot point of the scanning beam of the OCT apparatus at a plane of the pupil of the eye, wherein the iris plane module comprises:
- a light source operationally coupled to a cylindrical lens, the light source to project an illumination line onto an iris of an eye;
- a camera to capture a sequence of images of the eye;
- a processor to analyze the sequence of images of the eye to measure the sharpness of the illumination line; and
- a controller to adjust the position of a translational stage to maximize the sharpness of the illumination line.

2. The system of claim 1, further comprising a reference arm tuning module to adjust a reference arm length of the OCT apparatus.

3. The system of claim 2, further comprising an autofocusing system.

4. The system of claim 3, wherein the autofocusing system comprises an electrical tunable lens.

5. The system of claim 1, wherein the OCT apparatus is to detect eye plinking based on an OCT B-scan or micro-saccadic eye motion based on an OCTA B-scan and repeatedly re-acquire B-scans at a given location during the eye blinking or micro-saccadic eye motion.

6. The system of claim 1, wherein the OCT apparatus is to detect flow in an imaged sample.

7. The system of claim 1, wherein the fixation target module comprises a video projection system.

8. The system of claim 1, wherein the fixation target module comprises a liquid crystal diode screen system.

9. The system of claim 1, wherein the eye centering module comprises:
- a camera to capture a sequence of images of an eye;
- a processor to analyze the sequence of images of the eye to identify the location of a pupil center; and
- a controller to adjust the position of a translational stage to align the pupil center of the eye with the OCT apparatus.

10. The system of claim 1, wherein the light source is a light emitting diode.

11. A computer-based method comprising:
- scanning a sample using an optical coherence tomography (OCT) system to acquire a first OCT angiography (OCTA) scan and a second OCTA scan;
- generating, using one or more processors, a first en face angiogram from the first OCTA scan;
- generating, using the one or more processors, a second en face angiogram from the second OCTA scan;
- applying, using the one or more processors, a bias field correction to the first en face angiogram and to the second en face angiogram;
- detecting, using the one or more processors, motion lines in the first and second en face angiograms;
- dividing, using the one or more processors, the first and second en face angiograms into micro-saccade-free strips at the detected motion lines; and
- registering, using the one or more processors, a pair of overlapping micro-saccade-free strips, thereby generating a pair of aligned micro-saccade-free strips.

12. The method of claim 11, wherein applying the bias field correction comprises:
- applying a filter to an en face reflectance image; and
- correcting a reflectance-dependence of the en face angiogram.

13. The method of claim 12, wherein the filter is a Gaussian filter.

14. The method of claim 13, wherein the Gaussian filter has a standard deviation between 50 and 150 pixels.

15. The method of claim 12, wherein correcting the reflectance-dependence of the en face angiogram is performed according to:

$$D'(x, y) = D(x, y) * \frac{\text{Mean}(G(S))}{G(S(x, y))}$$

$$(x = 1, 2, 3, \ldots, X; y = 1, 2, 3, \ldots, Y)$$

where X×Y is a size of the en face angiogram, Mean(G(S)) is a mean value of the bias field, D(x,y) is the en face angiogram and G(S(x,y)) is the bias field by filtering en face reflectance image.

16. The method of claim 11, wherein detecting motion lines in the en face angiogram comprises: stabilizing decorrelation values in the en face angiogram by a mean value; increasing contrast of a capillary vascular network in the en face angiogram; increasing connectivity of the capillary vascular network in the en face angiogram; and removing lines in the en face angiogram having a respective line metric that exceeds a threshold.

17. The method of claim 11, wherein increasing contrast of a capillary vascular network in the en face angiogram is performed using a local histogram equalization method.

18. The method of claim 17, wherein the local histogram equalization method uses a 5×5 pixel grid.

19. The method of claim 16, wherein increasing connectivity of a capillary vascular network in the en face angiogram is performed using a Gabor filter.

20. The method of claim 16, wherein the line metric is mean or median decorrelation value of the line.

21. The method of claim 20, wherein the threshold is between 1.25 and 1.75 times the mean or the median decorrelation value of the en face angiogram.

22. The method of claim 11, wherein registering the pair of overlapping micro-saccade-free strips comprises:
- registering by gross alignment the pair of overlapping micro-saccade-free strips, thereby generating a pair of gross-aligned micro-saccade-free strips; and
- registering by fine alignment the pair of gross-aligned micro-saccade-free strips.

23. The method of claim 22, wherein registering by gross alignment the pair of overlapping micro-saccade-free strips comprises:
- determining a first strip and a second strip having maximum overlap;
- identifying large vessels the first strip and the second strip; and
- calculating a rigid transformation that aligns the large vessels in the first strip to the large vessels in the second strip.

24. The method of claim 23, wherein identifying large vessels in a strip comprises identifying pixels having a decorrelation value 1.3 times greater than the mean decorrelation value of said strip.

25. The method of claim 22, wherein registering by fine alignment the pair of overlapping micro-saccade-free strips comprises: increasing contrast of a capillary network in a first strip and a second strip; identifying small vessels the first strip and the second strip; calculating a non-rigid deformation transformation that aligns the small vessels in the first strip to the small vessels in the second strip.

26. The method of claim 25, wherein increasing contrast of the capillary network is performed by applying a multiscale vessel enhancement filter.

27. The method of claim 25, wherein identifying small vessels in the first strip and the second strip comprises identifying pixels having a decorrelation value between 0.6 and 1.3 times the mean decorrelation value of the respective first or second strip.

28. The method of claim 25, wherein the non-rigid deformation transformation is calculated using a B-spline free-form deformation algorithm.

29. The method of claim 11, further comprising:
repeating the registering of additional pairs of the microsaccade free strips to obtain a registered OCTA volume;
obtaining a structural optical coherence tomography (OCT) volume;
translating A-lines of the structural OCT volume based on the registered OCT to obtain a translated volumetric OCT;
rebuilding a boundary of the translated volumetric OCT; and
performing axial registration of the translated volumetric OCT based on the rebuilt boundary.

30. The method of claim 29, further comprising:
performing within-frame registration on the axially registered volumetric OCT based on cross-sectional OCTA to obtain a merged volumetric OCT+OCTA.

31. The method of claim 29, wherein the boundary is an inner limiting membrane (ILM) boundary.

32. The method of claim 29, wherein performing axial registration of the translated volumetric OCT based on the rebuilt volume comprises translating A-lines of the translated volumetric OCT based on a displacement between the rebuilt boundary and a corresponding boundary in the respective A-line.

* * * * *